United States Patent
Kang et al.

(10) Patent No.: US 10,520,442 B2
(45) Date of Patent: Dec. 31, 2019

(54) NANOGAP STRUCTURE HAVING ULTRASMALL VOID BETWEEN METAL CORES AND MOLECULAR SENSING APPARATUS AND METHOD USING THE SAME, AND METHOD FOR PREPARING THE NANOGAP STRUCTURE BY SELECTIVE ETCHING

(71) Applicant: Industry-University Cooperation Foundation Sogang University, Seoul (KR)

(72) Inventors: Taewook Kang, Seoul (KR); Yuna Sin, Seoul (KR)

(73) Assignee: Industry-University Cooperation Foundation Sogang University, Seoul (KR)

( * ) Notice: Subject to any disclaimer, the term of this patent is extended or adjusted under 35 U.S.C. 154(b) by 0 days.

(21) Appl. No.: 15/192,327

(22) Filed: Jun. 24, 2016

(65) Prior Publication Data
US 2016/0377549 A1  Dec. 29, 2016

(30) Foreign Application Priority Data
Jun. 24, 2015  (KR) .................... 10-2015-0090073

(51) Int. Cl.
| | | |
|---|---|---|
| *G01N 21/65* | (2006.01) | |
| *B82Y 40/00* | (2011.01) | |
| *G03F 7/00* | (2006.01) | |

(52) U.S. Cl.
CPC ............ *G01N 21/658* (2013.01); *B82Y 40/00* (2013.01); *G03F 7/00* (2013.01)

(58) Field of Classification Search
CPC .. G01N 21/658; G01N 21/554; G01N 21/553; G01N 2021/655; G03F 7/00; B82Y 40/00; B82Y 30/00
See application file for complete search history.

(56) References Cited

U.S. PATENT DOCUMENTS 7,381,465 B2 * 6/2008 Torimoto ................. B01J 13/02
                                                        427/215
8,208,136 B2 * 6/2012 Ivanov ................. G01N 21/658
                                                        356/301

(Continued)

FOREIGN PATENT DOCUMENTS

CN      104634935 A  *  5/2015
JP      2004299011 A     10/2004

(Continued)

OTHER PUBLICATIONS

"Plasmonic nature of van der Waals forces between nanoparticles" to Klimov et al. Plasmonics 4, 31 (2009).*

(Continued)

*Primary Examiner* — Mohamed K Amara
(74) *Attorney, Agent, or Firm* — Sughrue Mion, PLLC

(57) ABSTRACT

By forming a monolayer of metal core-shell nanoparticles, transferring the monolayer to various substrates and removing the shells surrounding the particles by way of selective etching, it is possible to form large-area uniform nanogap structures very easily. In addition, a nanogap is formed by an ultrasmall void having no limitation in diffusion between metal cores through Van der Waals interaction between metal core particles, as the etching proceeds. It is possible to enhance a near-field significantly around the nanogap structure.

13 Claims, 36 Drawing Sheets

(56) References Cited

U.S. PATENT DOCUMENTS

| | | | | |
|---|---|---|---|---|
| 8,269,963 | B2* | 9/2012 | Ou | G01N 21/658 356/301 |
| 8,372,295 | B2* | 2/2013 | Millward | B81C 1/00031 216/2 |
| 8,420,530 | B2* | 4/2013 | Thet | B82Y 10/00 257/774 |
| 8,462,334 | B2* | 6/2013 | Lu | B05D 1/204 356/301 |
| 8,558,304 | B2* | 10/2013 | Chen | G03F 7/0754 257/325 |
| 8,753,526 | B2 | 6/2014 | Yoon et al. | |
| 8,889,226 | B2* | 11/2014 | Walker | B22D 19/08 427/248.1 |
| 9,011,705 | B2* | 4/2015 | Shah | G01N 21/554 216/41 |
| 9,245,671 | B2* | 1/2016 | Simpson | H01B 13/14 |
| 9,346,913 | B2* | 5/2016 | Yan | C08G 73/0688 |
| 9,379,238 | B2* | 6/2016 | Larrieu | B82Y 10/00 |
| 9,440,224 | B2* | 9/2016 | Goia | B01J 23/892 |
| 9,476,785 | B2* | 10/2016 | Ivanov | B82Y 30/00 |
| 9,633,685 | B2* | 4/2017 | Kumar | G11C 13/048 |
| 9,638,625 | B2* | 5/2017 | Kim | G01N 21/658 |
| 9,678,014 | B2* | 6/2017 | Huang | G01N 21/554 |
| 9,777,372 | B2* | 10/2017 | Oh | C23C 16/45525 |
| 9,903,616 | B2* | 2/2018 | Chueh | C09K 5/14 |
| 9,989,677 | B2* | 6/2018 | Shalaev | G02B 1/002 |
| 9,993,185 | B2* | 6/2018 | Walavalkar | A61B 5/1459 |
| 2003/0015428 | A1* | 1/2003 | Becker | B03C 5/005 204/547 |
| 2003/0119057 | A1* | 6/2003 | Gascoyne | B82Y 30/00 435/7.1 |
| 2003/0158474 | A1* | 8/2003 | Scherer | B82Y 15/00 600/409 |
| 2006/0182966 | A1* | 8/2006 | Lee | B82Y 30/00 428/375 |
| 2008/0260941 | A1* | 10/2008 | Jin | B01J 35/0013 427/126.4 |
| 2009/0046362 | A1* | 2/2009 | Guo | B82Y 10/00 359/485.05 |
| 2010/0054981 | A1* | 3/2010 | Liu | B22F 1/0018 419/19 |
| 2010/0116656 | A1* | 5/2010 | Garcia Tello | G01N 27/44791 204/450 |
| 2010/0117138 | A1* | 5/2010 | Huerta | B82Y 10/00 257/324 |
| 2010/0124160 | A1* | 5/2010 | Kamiguchi | B82Y 10/00 369/112.24 |
| 2010/0218287 | A1* | 8/2010 | Nakata | G01Q 70/12 850/6 |
| 2011/0003279 | A1* | 1/2011 | Patel | G01D 3/10 435/5 |
| 2011/0084252 | A1* | 4/2011 | Wu | B82Y 30/00 257/40 |
| 2012/0052259 | A1* | 3/2012 | Kotake | H01L 51/0013 428/195.1 |
| 2012/0115245 | A1* | 5/2012 | Hasegawa | B82Y 15/00 436/501 |
| 2013/0172207 | A1* | 7/2013 | Dai | G01N 33/553 506/9 |
| 2013/0182258 | A1* | 7/2013 | Amako | G01N 21/55 356/445 |
| 2013/0209780 | A1* | 8/2013 | Poxson | C23C 14/083 428/312.6 |
| 2013/0278930 | A1* | 10/2013 | Liu | G01N 21/718 356/318 |
| 2013/0330839 | A1 | 12/2013 | Suh et al. | |
| 2014/0050851 | A1* | 2/2014 | Kagan | H01B 1/06 427/250 |
| 2014/0158946 | A1* | 6/2014 | Wu | H01B 1/24 252/511 |
| 2014/0224673 | A1* | 8/2014 | Alocilja | C12Q 1/6811 205/780.5 |
| 2014/0234226 | A1 | 8/2014 | Mahmoudi et al. | |
| 2014/0347661 | A1* | 11/2014 | Kim | G01N 21/658 356/301 |
| 2014/0374581 | A1 | 12/2014 | Dionne et al. | |
| 2015/0182641 | A1* | 7/2015 | Tan | A61K 49/0002 424/9.32 |
| 2015/0201837 | A1* | 7/2015 | Song | A61B 5/0002 600/345 |
| 2015/0253321 | A1* | 9/2015 | Chou | G01N 33/54366 435/5 |
| 2015/0375180 | A1* | 12/2015 | Rybtchinski | C08G 61/122 556/31 |
| 2016/0069810 | A1* | 3/2016 | Walavalkar | G01N 21/658 356/301 |
| 2016/0116402 | A1* | 4/2016 | Chen | G01N 21/3581 250/343 |
| 2016/0184899 | A1 | 6/2016 | Kang et al. | |
| 2016/0215171 | A1* | 7/2016 | Marcellan | A61K 8/25 |
| 2017/0123291 | A1* | 5/2017 | Vampa | G02F 1/353 |
| 2017/0260426 | A1* | 9/2017 | Zhang | C08L 25/06 |
| 2018/0151564 | A1* | 5/2018 | Lee | H01L 21/823481 |

FOREIGN PATENT DOCUMENTS

| | | |
|---|---|---|
| KR | 10-2009-0050142 A | 5/2009 |
| KR | 1020120017917 A | 2/2012 |
| KR | 10-2012-0056024 A | 6/2012 |
| KR | 1020150011727 A | 2/2015 |

OTHER PUBLICATIONS https://en.wikipedia.org/wiki/Van_der_Waals_force.*

"Nanocap array of Au:Ag composite for surface-enhanced Raman scattering", to Zhang et al. (Spect. Acta Part A, 152 (2016) 461-467.*

Wang et al. "Au/Ag bimetal nanogap arrays with tunable morphologies for surface-enhanced Raman scattering", RSC Adv. 2015, 5, 7454 (published on Dec. 22, 2014).* https://www.dictionary.com/browse/capping.*

Kyle D. Osberg et al.;"Dispersible Gold Nanorod Dimers with Sub-5 nm Gaps as Local Amplifiers for Surface-Enhanced Raman Scattering," Nano Letter, 2012, vol. 12, pp. 3828-3832.

Kristin L. Wustholz et al.; "Structure-Activity Relationships in Gold Nanoparticle Dimers and Trimers for Surface-Enhanced Raman Spectroscopy," Journal of the American Chemical Society, 2010, vol. 132, pp. 10903-10910.

Dong-Kwon Lim et al.; "Highly uniform and reproducible surface-enhanced Raman scattering from DNA-tailorable nanoparticles with 1-nm interior gap," Nature Nanotechnology, 2011, vol. 6, pp. 452-460.

Bo Zhang et al.; "Shrink induced nanostructures for energy conversion efficiency enhancement in photovoltaic devices," Applied Physics Letters, 2013, vol. 103, 023104 (6 pages total).

De-Yin Wu et al.; "Photon-driven charge transfer and photocatalysis of p-aminothiophenol in metal nanogaps: a DFT study of SERS," Chem. Commun., 2011, vol. 47, pp. 2520-2522.

Ryoko Watanabe-Tamakai et al.; "DNA-Templating Mass Production of Gold Trimer Rings for Optical Metamaterials," Journal of Physical Chemistry, 2012, vol. 116, pp. 15028-15033.

Dong-Kwon Lim et al.; "Nanogap-engineerable Raman-active nanodumbbells for single-molecule detection," Nature Materials, 2010, vol. 9, pp. 60-67.

Srdjan S. Acimovic et al.; "Plasmon Near-Field Coupling in Metal Dimers as a Step toward Single-Molecule Sensing," ACS Nano, 2009, vol. 3, No. 5, pp. 1231-1237.

Makusu Tsutsui et al.; "Identifying single nucleotides by tunnelling current," Nature Nanotechnology, 2010, vol. 5, pp. 286-290.

Huigao Duan et al.; "Free-standing sub-10 nm nanostencils for the definition of gaps in plasmonic antennas," Nanotechnology, 2013, vol. 24, 185301 (9 pages total).

Hyungsoon Im et al.; "Vertically Oriented Sub-10-nm Plasmonic Nanogap Arrays," Nano Letters, 2010, vol. 10, pp. 2231-2236.

(56) References Cited

OTHER PUBLICATIONS

Hyungsoon Im et al.; "Self-Assembled Plasmonic Nanoring Cavity Arrays for SERS and LSPR Biosensing," Advanced Materials, 2013, vol. 25, pp. 2678-2685.
Yasuhisa Naitoh et al.; "Self-Aligned Formation of Sub 1 nm Gaps Utilizing Electromigration during Metal Deposition," ACS Applied Materials & Interfaces, 2013, vol. 5, pp. 12869-12875.
Joseph B. Herzog et al.; "Dark Plasmons in Hot Spot Generation and Polarization in Interelectrode Nanoscale Junctions," Nano Letters, 2013, vol. 13, pp. 1359-1364.
Daniel R. Ward et al.; "Optical rectification and field enhancement in a plasmonic nanogap," Nature Nanotechnology, 2010, vol. 5, pp. 732-736.
Huigao Duan et al.; "Direct and Reliable Patterning of Plasmonic Nanostructures with Sub-10-nm Gaps," ACS Nano, 2011, vol. 5, No. 9, pp. 7593-7600.
Nahla A. Hatab et al.; "Free-Standing Optical Gold Bowtie Nanoantenna with Variable Gap Size for Enhanced Raman Spectroscopy," Nano Letters, 2010, vol. 10, pp. 4952-4955.
Jibin Song et al.; "SERS-Encoded Nanogapped Plasmonic Nanoparticles.. Growth of Metallic Nanoshell by Templating Redox-Active Polymer Brushes," Journal of the American Chemical Society, 2014, vol. 136, pp. 6838-684.
Jeong-Wook Oh et al.; "Thiolated DNA-Based Chemistry and Control in the Structure and Optical Properties of Plasmonic Nanoparticles with Ultrasmall Interior Nanogap," Journal of the American Chemical Society, 2014, vol. 136, pp. 14052-14059.
Hui Wang et al.; "Nanosphere Arrays with Controlled Sub-10-nm Gaps as Surface-Enhanced Raman Spectroscopy Substrates," Journal of the American Chemical Society, 2005, vol. 127, pp. 14992-14993.
Xiang Lan et al.; "DNA-Directed Gold Nanodimers with Tailored Ensemble Surface-Enhanced Raman Scattering Properties," ACS Applied Materials & Interfaces, 2013, vol. 5, pp. 10423-10427.
Ximei Qian et al.; "Stimuli-Responsive SERS Nanoparticles.. Conformational Control of Plasmonic Coupling and Surface Raman Enhancement," Journal of the American Chemical Society, 2009, vol. 131, pp. 7540-7541.
Shuming Nie et al.; "Probing Single Molecules and Single Nanoparticles by Surface-Enhanced Raman Scattering," Science, 1997, vol. 275, pp. 1102-1106.
Honglin Liu et al.; "Three-Dimensional and Time-Ordered Surface-Enhanced Raman Scattering Hotspot Matrix," Journal of the American Chemical Society, 2014, vol. 136, pp. 5332-5341.
Samuel L. Kleinman et al.; "Creating, characterizing, and controlling chemistry with SERS hot spots," Physical Chemistry Chemical Physics, 2013, vol. 15, No. 1, pp. 21-36.
Jian Feng Li et al.; "Shell-isolated nanoparticle-enhanced Raman spectroscopy," Nature, 2010, vol. 464, pp. 392-395.
Thearith Ung et al.; "Optical Properties of Thin Films of Au@SiO2 Particles," J. Phys. Chem., B 2001, vol. 105, pp. 3441-3452.
Francois Reincke et al.; "Spontaneous Assembly of a Monolayer of Charged Gold Nanocrystals at the Water-Oil Interface," Angew. Chem. Int. Ed., 2004, vol. 43, pp. 458-462.
Yong-Jun Li et al.; "A Universal Approach for the Self-Assembly of Hydrophilic Nanoparticles into Ordered Monolayer Films at a Toluene-Water Interface," Angew. Chem. Int. Ed., 2006, vol. 45, pp. 2537-2539.
Yong-Kyun Park et al.; "Directing Close-Packing of Midnanosized Gold Nanoparticles at a Water-Hexane Interface," Chem. Mater., 2008, vol. 20, pp. 2388-2393.
David C. Duffy et al.; "Rapid Prototyping of Microfluidic Systems in Poly (dimethylsiloxane)," Analytical Chemistry, 1998, vol. 70, No. 23, pp. 4974-4984.
Zhi-Guang Guo et al.; "Sticky superhydrophobic surface," Applied Physics Letters, 2007, vol. 90, 223111 (4 pages total).
Yuzhe Ding et al.; "Universal Nanopatternable Interfacial Bonding," Advanced Materials, 2011, vol. 23, pp. 5551-5556.
Hyeon Don Song et al.; "On-Chip Colorimetric Detection of Cu2+ Ions via Density-Controlled Plasmonic Core-Satellites Nanoassembly," Analytical Chemistry, 2013, vol. 85, pp. 7980-7986.
Sebastian P. Scheeler et al.; "Plasmon Coupling in Self-Assembled Gold Nanoparticle-Based Honeycomb Islands," Journal of Physical Chemistry, 2013, vol. 117, pp. 18634-18641.
Weian Zhao et al.; "Design of Gold Nanoparticle-Based Colorimetric Biosensing Assays," ChemBioChem, 2008, vol. 9, pp. 2363-2371.
Younjin Min et al.; "The role of interparticle and external forces in nanoparticle assembly," Nature Materials, 2008, vol. 7, pp. 527-538.
Frens, G. et al.; "Controlled Nucleation for the Regulation of the Particle Size in Monodisperse Gold Suspensions," Nature Physical Science, 1973, vol. 241, pp. 20-22.

\* cited by examiner

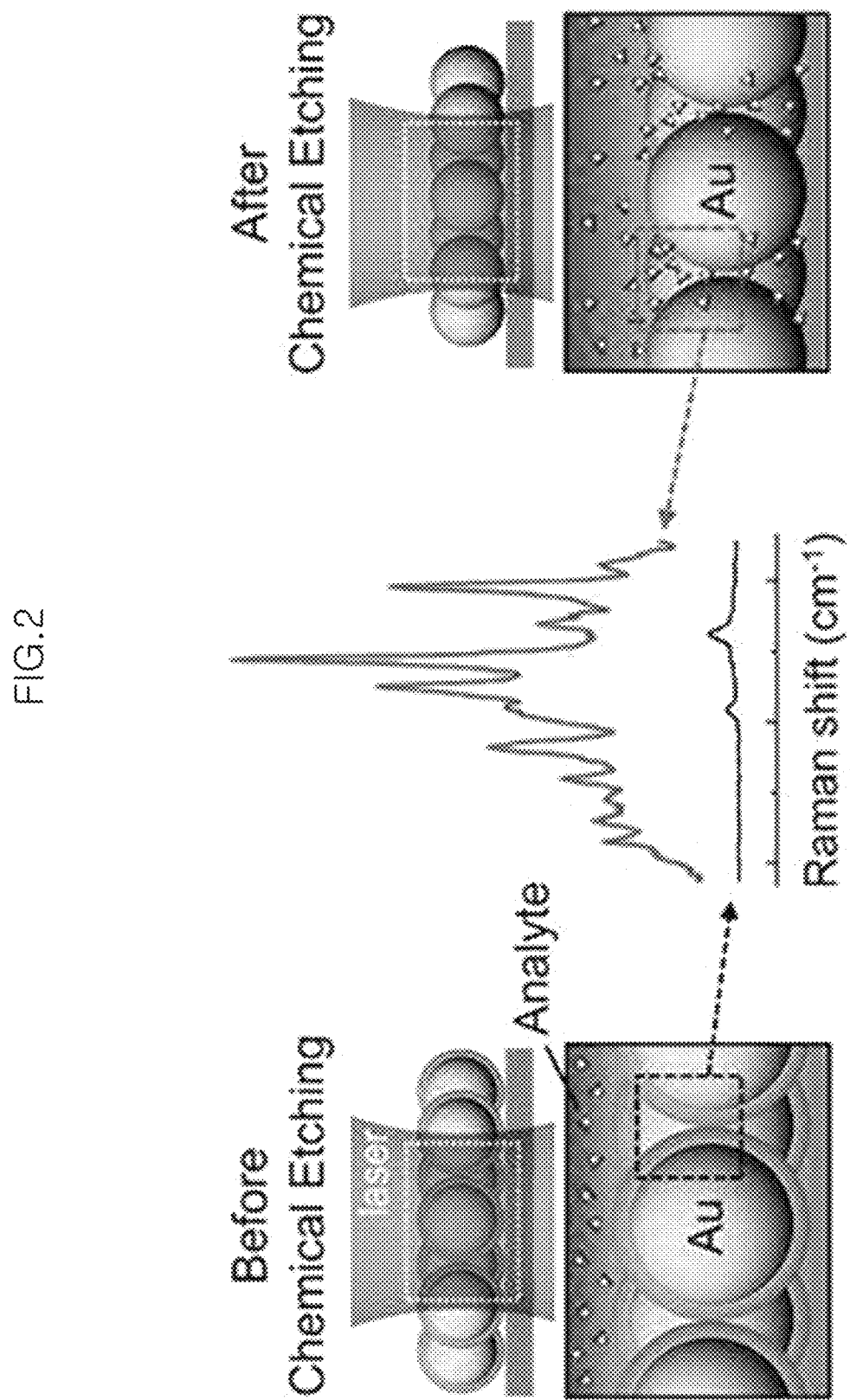

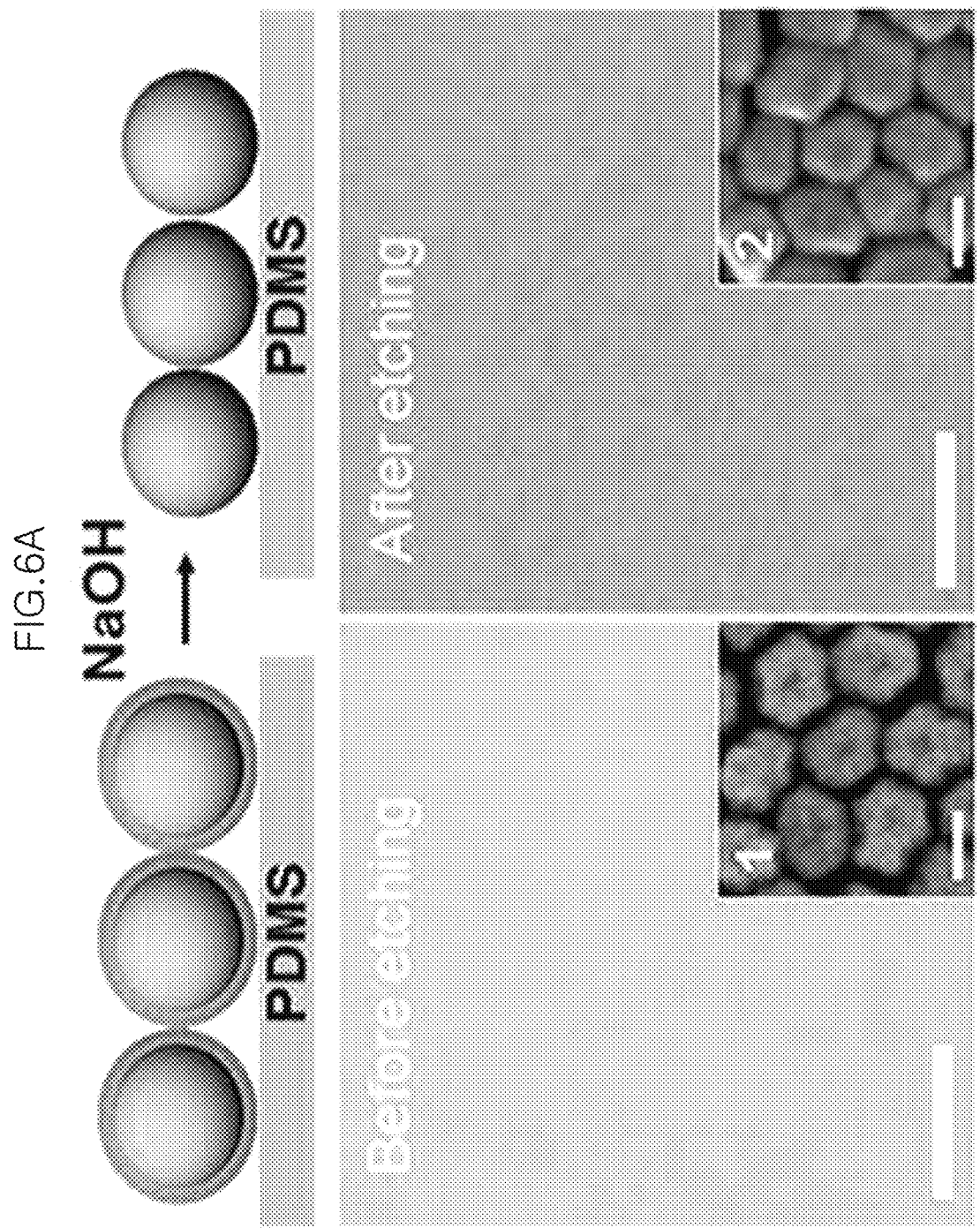

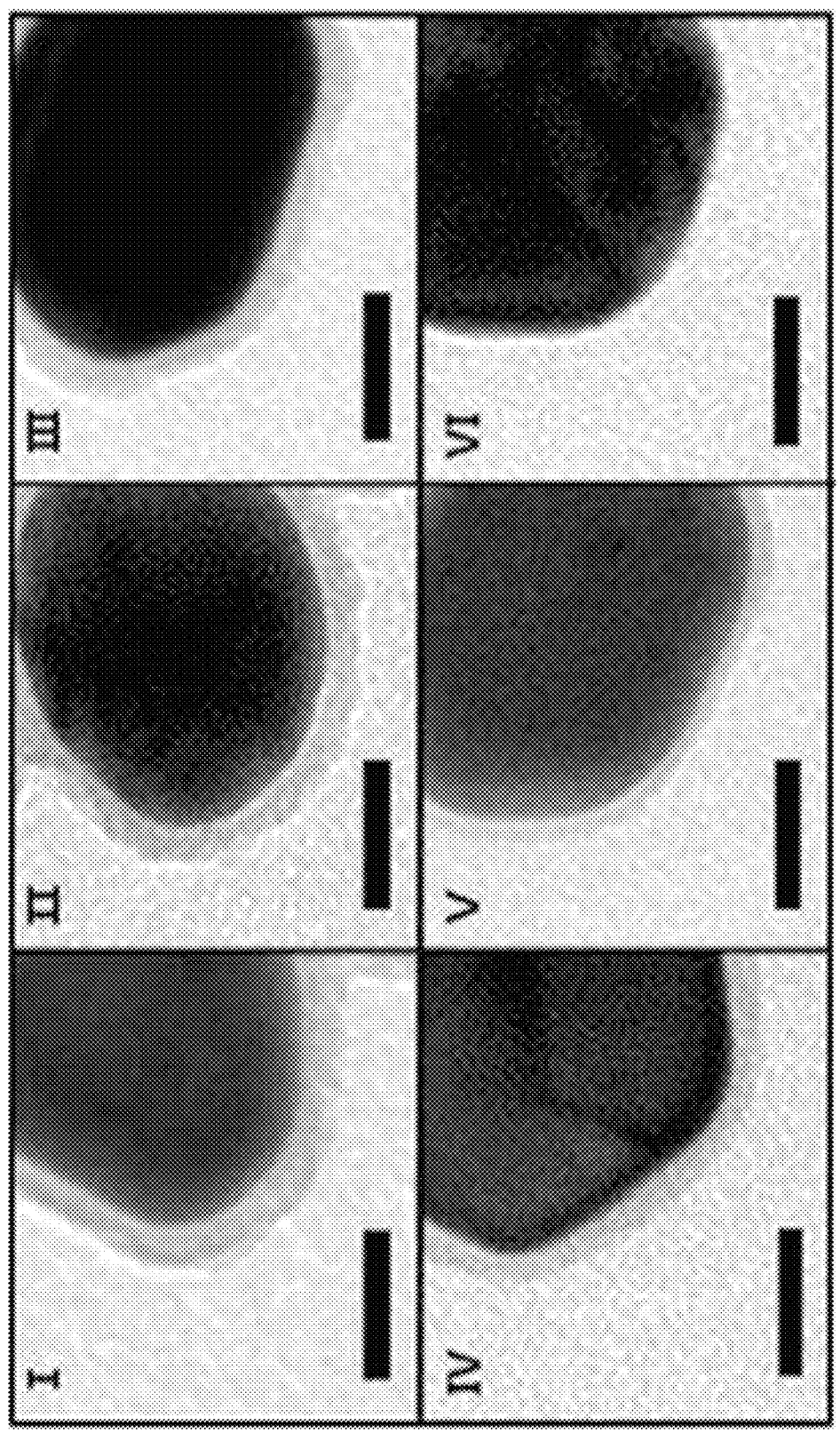

NANOGAP STRUCTURE HAVING ULTRASMALL VOID BETWEEN METAL CORES AND MOLECULAR SENSING APPARATUS AND METHOD USING THE SAME, AND METHOD FOR PREPARING THE NANOGAP STRUCTURE BY SELECTIVE ETCHING

CROSS-REFERENCE TO RELATED APPLICATION

This application claims a priority of Korean Patent Application No. 10-2015-0090073, filed on Jun. 24, 2015, and all the benefits accruing therefrom under 35 U.S.C. § 119, the contents of which in their entirety are herein incorporated by reference.

BACKGROUND

1. Field

The present disclosure relates to a nanogap structure having an ultrasmall void between metal cores and a molecular sensing apparatus and method using the same, and a method for preparing the nanogap structure by selective etching.

2. Description of the Related Art

A nanogap (nanovoid) formed between two or more metallic nanostructures provides a space capable of localizing external optical energy and enables plasmonic binding between metallic nanoparticles to generate very high electromagnetic signal amplification. A metallic nanogap structure may be used widely in various fields, such as photovoltaics, photocatalysis, metamaterials, surface-enhanced spectroscopy, molecular sensing, or the like.

Typically, the methods for fabricating a metallic nanogap may be classified into lithography-based top-down approaches and bottom-up approaches.

The lithography-based top-down approaches may include fabricating a metallic nanogap through a sophisticated lithography process. For example, energy beam lithography or photolithography is used to irradiate a substrate with micro-/nano-scaled beams, thereby forming a metallic electrode pattern, which can be broken down through mechanical control or electromigration to realize nanometer-scaled gaps. In addition, a metallic layer may be deposited on a lithographically patterned template and the template is removed through a lift-off process to form gaps which have, for example, a sub-10 nm gap size.

Additionally, a nano-scaled thin alumina sacrificial layer may be deposited between two metallic layers through an atomic layer deposition process and the exposed unnecessary alumina may be etched chemically through an ion beam milling and a chemical etching to form nanogaps having a size corresponding to a thickness of the atomic layer deposited thin film.

Meanwhile, as alternative approaches to the above-mentioned top-down approaches, some methods for forming nanogap structures through bottom-up approaches have been suggested.

In theses bottom-up approaches, generally linker molecules, such as DNA, block copolymers or ligand molecules may be introduced between metallic nanoparticles as gap-directing molecules to form nanogaps having a size of several nanometers.

Further, as another alternative approach, nanogaps may be formed through a metallic nanoparticle aggregation phenomenon. Such bottom-up approaches are advantageous in that the size, density and interparticle distance of nanostructures can be controlled as compared to the top-down approaches.

However, according to the studies conducted by the present inventors, most lithography-based top-down approaches require the use of the newest micro-/nano-technology or expensive equipments, and thus are not suitable for forming large-area nanogap structures. Moreover, it is required to develop a process for reducing the cost needed for forming large-area nanogap structures.

Meanwhile, the bottom-up approaches should overcome the problems that they require a delicate control over chemical reaction conditions, have low reproducibility (in case of the metallic nanoparticle aggregation method: H. Liu, Z. Yang, L. Meng, Y. Sun, J. Wang, L. Yang, J. Liu, Z. Tian, J. Am. Chem. Soc. 2014, 136, 5332-5341), or are limited in diffusion of molecules to be sensed due to the linker molecules or gap-directing molecules present between metallic nanostructures.

SUMMARY

In exemplary embodiments, in an aspect, provided is a method for preparing a nanogap structure having an ultrasmall void between metal cores and a nanogap structure having an ultrasmall void between metal cores obtained thereby, which allow formation of large-area uniform nanogap structures with ease at low cost and also allow an easy reproduction, while avoiding the use of a delicate chemical reaction condition as required in case of the conventional bottom-up methods or the use of a complicated micro-/nano-technology or expensive equipment as required in case of the conventional top-down methods.

In exemplary embodiments, in another aspect, provided is a nanogap structure having an ultrasmall void between metal cores, which enables free diffusion of analyte molecules and is able to show a strong near-field enhancement, a method for preparing the same, and a molecular sensing apparatus and method capable of sensing a molecule with high sensitivity by using the nanogap structure.

In exemplary embodiments, there is provided a nanogap structure including an assembly of core particles in which shells are removed, wherein the assembly has a void formed between metal core particles and a nanogap is provided by the void.

In an exemplary embodiment, the assembly of the metal core particles may form a monolayer of the metal core particles.

In an exemplary embodiment, Van der Waals force may be exerted between metal core particles.

In an exemplary embodiment, the void may have a size smaller than a spacing distance by shell.

In an exemplary embodiment, the void may be an ultrasmall void having a size of 2 nm or less.

In an exemplary embodiment, the metal core may consist of at least one metal selected from the group consisting of Au, Ag, Cu, Pt and Pd.

In an exemplary embodiment, the metal core particles may have a diameter of 10-150 nm and the void may have a size of 1-2 nm.

In an exemplary embodiment, the nanogap provided by the void may show an additional enhancement factor as compared to the particles before the shells are removed.

In an exemplary embodiment, the nanogap provided by the void may show a near-field enhancement.

In an exemplary embodiment, the nanogap provided by the void may show a free diffusion of molecules without limitation in diffusion of molecules.

In exemplary embodiments, there is provided a method for preparing a nanogap structure, including removing shells from nanoparticles having metal cores and shells to form a void between metal core particles, wherein a nanogap is provide by the void.

In an exemplary embodiment, the method may include: forming a monolayer of nanoparticles having metal cores and shells; transferring the monolayer to a substrate; and removing the shells from the monolayer of nanoparticles having metal cores and shells and disposed on the substrate, by way of etching.

In an exemplary embodiment, the monolayer of nanoparticles having metal cores and shells may be formed by self-assembly at an air/liquid interface.

In an exemplary embodiment, the nanoparticles having metal cores and shells are introduced to a mixture of hexane with water which forms an interface, and ethanol is added thereto, and hexane is evaporated to form the monolayer of the nanoparticles having metal cores and shells at an air/water interface.

In an exemplary embodiment, the nanoparticles may have a close-packed structure in the monolayer.

In an exemplary embodiment, the metal core may consist of at least one metal selected from the group consisting of Au, Ag, Cu, Pt and Pd.

In an exemplary embodiment, the metal core particles may have a diameter of 10-150 nm.

In an exemplary embodiment, the shell may consist of at least one selected from the group consisting of Au, Ag, Cu, Pt, Pd, Si (silicon), $SiO_2$ (silica), Al, $Al_2O_3$ (aluminum oxide), PS (polystyrene), Ti (titanium) and $TiO_2$ (titanium dioxide).

In an exemplary embodiment, the shell may have a size of 1-20 nm.

In an exemplary embodiment, the substrate may be a solid substrate.

In an exemplary embodiment, the substrate may be a PDMS (polydimethylsiloxane) substrate, PMMA (poly(methylmethacrylate)) substrate, PS (polystyrene) substrate, Si (silicon) substrate, Ge (germanium) substrate, glass substrate or ITO (Indium tin oxide) substrate.

In an exemplary embodiment, the solid substrate may be chemically modified to improve a binding force with the nanoparticles.

In an exemplary embodiment, the etching may be at least one selected from chemical etching, ion beam etching and electron beam etching.

In an exemplary embodiment, the etching may be a chemical etching wherein a basic solution is provided to etch.

In exemplary embodiments, there are provided a molecular sensing apparatus including the nanogap structure and a molecular sensing method using the nanogap structure.

In an exemplary embodiment, an analyte molecule to be sensed may be a biomolecule in the molecular sensing apparatus.

In an exemplary embodiment, the molecular sensing apparatus may be an apparatus sensing Raman signals by using Surface Enhanced Raman spectroscopy (SERS).

According to the method for preparing a nanogap structure of the exemplary embodiments, it is possible to form large-area uniform nanogap structures with ease at low cost and to realize an easy reproduction, while avoiding a need for a delicate chemical reaction condition as required in case of the conventional bottom-up approaches, a problem related with reproducibility and use of a complicated micro-/nano-technology or expensive equipment as required in case of the conventional top-down approaches.

In addition, the nanogap structure according to the exemplary embodiments may allow free diffusion of analyte molecules without limitation in diffusion of analyte molecules, thereby providing a strong near-field enhancement. As a result, it is possible to sense/monitor/analyze analyte molecules with high sensitivity by using the nanogap structure without limitation in diffusion of analyte molecules.

BRIEF DESCRIPTION OF THE DRAWINGS

The above and other aspects, features and advantages of the disclosed example embodiments will be more apparent from the following detailed description taken in conjunction with the accompanying drawings in which:

FIG. 2 is a view illustrating a Raman enhancement effect of a nanogap structure by an ultrasmall void between metal cores after the etching of a shell in an example;

FIG. 6A shows a schematic view and photograph (left-side) of the monolayer of gold-core silica-shell nanoparticles (Au@SiO$_2$ nanoparticles) having a shell thickness of 5.0 nm on PDMS, and a schematic view and photograph (right-side) of the layer of Au core particles in which the shells are etched after carrying out etching for 150 minutes, in an example, wherein the inset image is a FESEM image;

FIG. 6B is an EFTEM image illustrating a change of silica shell in each of gold-core silica-shell nanoparticles (Au@SiO$_2$ nanoparticles) after various etching times, in an example;

FIG. 9A and FIG. 9B show SERS signals of the monolayer of gold-core silica-shell nanoparticles (Au@SiO$_2$ nanoparticles) on PDMS before and after the etching depending on the time of the silica etching (1 μM R6G), wherein FIG. 9A shows SERS signals at 0 min., 90 min., 110 min., 130 min., 150 min., and PDMS as viewed sequentially from the top, and FIG. 9B shows SERS signals of 5.0 nm shell, 2.5 nm shell, Before etching (2.5 nm shell), Before etching (5.0 nm shell) and PDMS, as viewed from sequentially the top;

DETAILED DESCRIPTION

Figure 1:
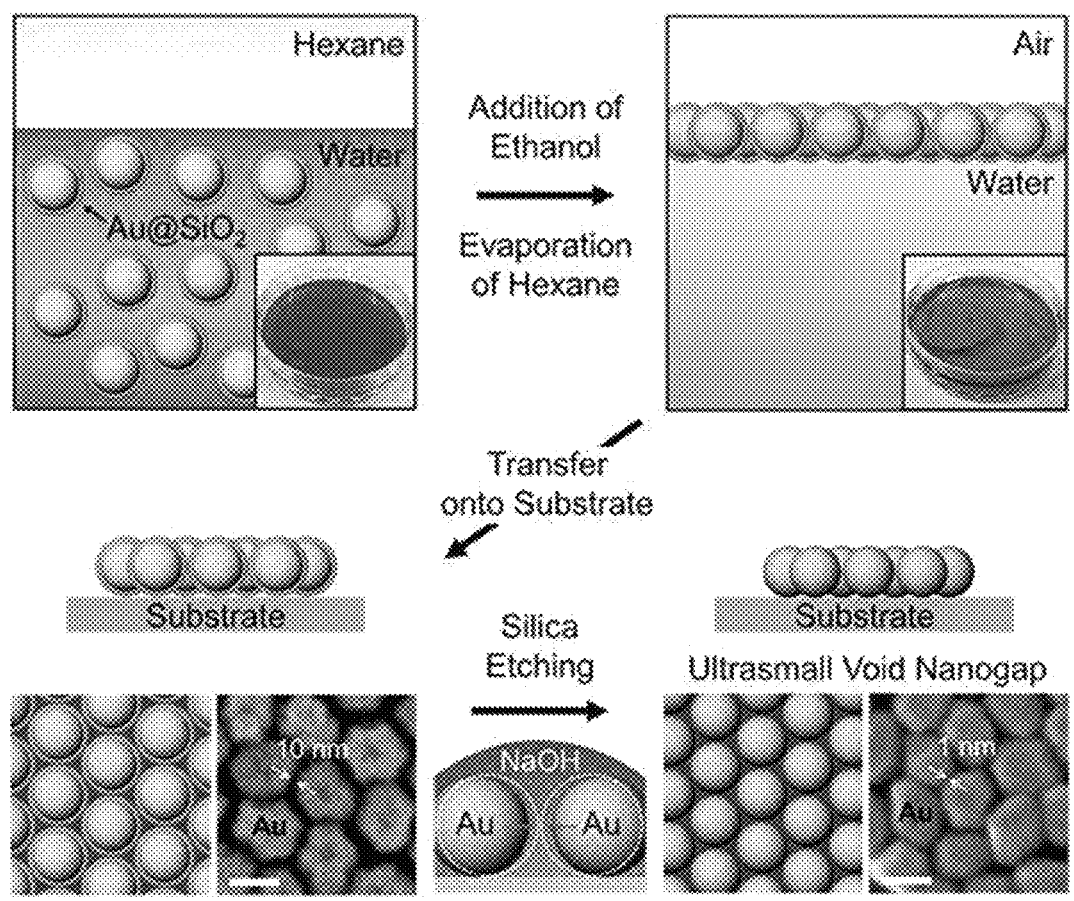
FIG. 1 is a schematic view illustrating a process for forming large-area uniform nanogap structures in an example.

Example embodiments are described more fully hereinafter. The disclosure may, however, be embodied in many different forms and should not be construed as limited to the example embodiments set forth herein. Rather, these example embodiments are provided so that this disclosure will be thorough and complete, and will fully convey the scope of the disclosure to those skilled in the art. In the description, details of features and techniques may be omitted to more clearly disclose example embodiments.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. Furthermore, the use of the terms a, an, etc. do not denote a limitation of quantity, but rather denote the presence of at least one of the referenced item. The terms "first," "second," and the like do not imply any particular order, but are included to identify individual elements. Moreover, the use of the terms first, second, etc. do not denote any order or importance, but rather the terms first, second, etc. are used to distinguished one element from another.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on the scope of the disclosure unless otherwise claimed. No language in the specification should be construed as indicating any non-claimed element as essential to the practice of the disclosure as used herein.

Definition of Terms

In the present disclosure, void means a vacant space formed by removing a shell between cores.

In the present disclosure, void size (dimension) means an interparticle distance between adjacent core particles.

In the present disclosure, interparticle distance means the shortest distance between neighboring particles, and may be determined by the shortest distance between neighboring particles which are measured, for example, from 10 particles (wherein particles having 6 neighboring particles may be selected as for the 10 particles). For example, such an interparticle distance may be determined through FESEM and EFTEM images as obviously understood by those skilled in the art.

In the present disclosure, ultrasmall void means a void having a size of 5 nm or less, 2 m or less, 1 nm or less, or 1-2 nm.

In the present disclosure, nano means a scale of 100 nm or less. However, nanogap means a gap having a size of 10 nm or less, 5 nm or less, 2 nm or less, 1 nm or less, or 1-2 nm.

In the present disclosure, limitation in diffusion of molecules means a limitation in diffusion movement of analyte molecules into an inner part of a gap. For example, the limitation in diffusion movement of analyte molecules into an inner part of a gap may occur when a space into which the analyte molecules can be diffused is limited due to linker molecules or gap-forming molecules etc. present between metallic nanostructures.

In the present disclosure, free diffusion means that diffusion is allowed without the limitation in diffusion of molecules in the vicinity of a nanogap.

In the present disclosure, selective etching means etching shells alone amongst cores and shells.

In the present disclosure, spacing distance by shell means a distance between cores spaced from each other by a shell when the core is surrounded with the shell.

In the present disclosure, when it is said that void size is smaller than the spacing distance by shell, it means that the void size between cores after the shell is removed becomes smaller than the spacing distance by shell between cores before the shell is removed.

In the present disclosure, citrate-stabilized means that the surface of metallic nanoparticles is coated with citrate ions in order to be dispersed in aqueous solution in a stable manner. Particularly, gold nanoparticles coated with negatively charged citrate ions have negative surface charges, and thus the particles are not aggregated with each other but are able to be in a stable mono-dispersed state by the electrostatic repulsion between particles due to the surface charges.

In the present disclosure, close-packed structure (or dense structure) means a layer of assembled particles in which the particles are packed while being adjacent to each other. It stands to reason that the term close-packed does not merely mean an ideal close-packed structure of ideal particles having a spherical particle shape and the same size. It is obviously apparent to those skilled in the art that particles having different sizes and shapes are also covered.

In the present disclosure, hexagonal close-packed structure does not merely mean an ideal hexagonal close-packed structure but also covers a structure of particles having different sizes and shapes, which is similar to a hexagonal close-packed structure.

In the present disclosure, molecular sensing means not only sensing of analyte molecules but also monitoring, analysis or the like of analyte molecules.

In the present disclosure, molecular sensing apparatus means various apparatuses for use in sensing/monitoring/analysis, etc. of molecules.

Description of Exemplary Embodiments

Hereinafter, the exemplary embodiments of the present invention will be explained in detail.

In exemplary embodiments of the present invention, there is provided a nanogap structure including an assembly of core particles from which shells are removed, wherein the assembly has a void formed between one metal core particle and another metal core particle and the a nanogap is provided by the void.

Van der Waals force is exerted between metal core particles. As described hereinafter, such Van der Waals force further narrows a void spacing between metal cores after shells are removed.

In an exemplary embodiment, it is preferred that the assembly of particles is particularly a monolayer of particles. When the particles form such a monolayer of particles, it can be transferred to a solid substrate, thereby facilitating formation of large-area uniform metallic nanogap structures on various solid substrates.

In addition, such a nanogap void can be reproduced more easily. That is, in exemplary embodiments of the present invention, since the monolayer is a metallic nanogap structure having a two-dimensional uniform arrangement, it is easy to overcome the problem of low reproducibility occurring in the methods for forming nanogaps (particularly, in case of the methods based on metallic nanoparticle aggregation). Further, it is also possible to show higher reproducibility when forming the void gap structures.

In addition, when considering the applicability to molecular sensing, such formation of a monolayer of nanoparticles may enable molecular sensing with higher sensitivity and the monolayer having a uniform arrangement may ensure reproducibility of sensed signals.

In an exemplary embodiment, the void may be an ultrasmall void having a size of 5 nm or less, preferably 2 nm or less, more preferably 1 nm or less, or for example 1-2 nm.

In an exemplary embodiment, the nanogap may provide an additional enhancement factor by virtue of the void as compared to the structure before etching the shells. In addition, the nanogap may provide a near-field enhancement. Such near-field enhancement may be determined by Raman signals. Further, a free diffusion of molecules is possible without limitation in diffusion of molecules at the nanogap formed by the void.

Meanwhile, in exemplary embodiments of the present invention, there is provided a method for preparing a nanogap structure which includes removing shells from nanoparticles having metal cores and shells to form a void between metal core particles, wherein a nanogap is provided by the void.

In an exemplary embodiment, the method may include: forming a monolayer of nanoparticles having metal cores and shells; and removing the shells from the monolayer of nanoparticles having metal cores and shells by way of etching.

More particularly, in an exemplary embodiment, the method may include: forming a monolayer of nanoparticles having metal cores and shells; transferring the monolayer to a substrate; and removing the shells from the monolayer of nanoparticles which have metal cores and shells and are disposed on the substrate by way of etching. When using a substrate as mentioned above, it is possible to structuralize nanomaterials, which is advantageous for commercialization of nanostructures. As described hereinafter, in exemplary embodiments of the present invention, the monolayer is transferred to the substrate and the void nanogap is formed through etching. According to this, it is possible to obtain an effect of very highly amplifying electromagnetic signals resulting from a decrease in distance between core particles and to produce a large-area uniform void nanogaps having no limitation in diffusion.

In a non-limiting example, a monolayer of nanoparticles having metal cores and shells may be formed by self-assembly at an air/liquid interface. More particularly, for example, the nanoparticles having metal cores and shells are introduced to a mixture of two different liquids (such as hexane as a first liquid to be evaporated afterwards and water as a second liquid to be left without evaporation) forming an interface, and a third liquid (such as ethanol) is added thereto so that the surface charge density of the nanoparticles may be reduced, and then the first liquid, hexane, is evaporated to form a monolayer of nanoparticles having metal cores and shells at the air/water interface.

In an exemplary embodiment, the monolayer may have a close-packed structure of nanoparticles. For example, the nanoparticles may have a hexagonal close packed structure.

In an exemplary embodiment, the metal core is not particularly limited but may consist of, for example, at least one metal selected from the group consisting of Au, Ag, Cu, Pt and Pd, and may consist of particularly Au.

In an exemplary embodiment, the metal core may have a diameter of 10-150 nm.

In an exemplary embodiment, the shell is not particularly limited but may consist of at least one selected from the group consisting of Au, Ag, Cu, Pt, Pd, Si (silicon), $SiO_2$ (silica), Al, $Al_2O_3$ (aluminum oxide), PS (polystyrene), Ti (titanium) and $TiO_2$ (titanium dioxide), may consist of particularly silica.

In an exemplary embodiment, the shell may have a size of 1-20 nm.

In an exemplary embodiment, the substrate may be any one of various substrates and may be a solid substrate. In a non-limiting example, the substrate may be a polymer substrate, such as a PDMS (polydimethyl siloxane), PMMA (poly(methyl methacrylate)) or PS (polystyrene) substrate, a semiconductor substrate, such as a Si (silicon) or Ge (germanium) wafer, a glass substrate or an ITO (indium tin oxide) substrate. Such a substrate may be selected adequately depending on the application of a nanogap structure (application of a nanogap structure may be varied with properties of a substrate).

In an exemplary embodiment, the substrate may be chemically modified to improve the adhesion force to nanoparticles.

In an exemplary embodiment, the etching may be chemical etching. In addition to chemical etching, the etching may include ion beam etching and electron beam etching. For example, the chemical etching may be an etching wherein a basic solution is provided to etch. Examples of the basic solution may include NaOH (sodium hydroxide) and KOH (potassium hydroxide).

After the nanoparticles are subjected to etching, the shells are removed and the gap between cores is narrowed by Van der Waals force to become smaller than the spacing distance formed by the shell between cores (for example, the gap is narrowed to about 5 nm or less, about 2 nm or less, or about 1-2 nm).

In exemplary embodiments of the present invention, there is provided a molecular sensing apparatus including the nanogap structure.

In exemplary embodiments of the present invention, there is provided a molecular sensing method using the nanogap structure.

In an exemplary embodiment, when carrying out molecule sensing by using the nanogap structure, there is no limitation in diffusion of analyte molecules.

Herein, various analyte molecules which can be SERS target probes may be applied as the analyte molecules and the apparatus and method may be used for sensing of various biomolecules.

As described above, in exemplary embodiments of the present invention, an assembly of metal core-shell nanoparticles, such as a monolayer of metal core-shell nanoparticles, is formed and transferred to various substrates according to needs, and then the shells surrounding the particles are removed through selective etching so that large-area nanogap structures may be formed very easily. In addition, it is determined that nanogaps are formed by ultrasmall voids through the interaction between metal core particles, as the etching proceeds. Particularly, it is demonstrated through reflectance spectrometry that plasmonic coupling is reinforced as the distance between metal core nanoparticles is decreased. In addition, it is shown that near field in the vicinity of nanogap structures can be enhanced significantly.

In addition, it is demonstrated that when the resultant nanogap structures are applied to surface enhanced Raman spectroscopy (SERS) which is an ultrasensitive analysis technology, it is possible to show an additional enhancement factor, for example, at least 1,000-10,000 times higher than the core-shell nanoparticle structures before etching and to obtain high electromagnetic signal amplification. As a result, it is shown that the nanogap structures and the method for producing the same according to exemplary embodiments of the present invention have applicability to molecular sensing and improvement in signal sensing.

Hereinafter, the present disclosure will be described in detail through examples. However, the following examples are for illustrative purposes only and it will be apparent to those of ordinary skill in the art that the scope of the present disclosure is not limited by the examples.

Examples

In this experiment, gold-silica core-shell nanoparticles are used to obtain nanogap structures. For this, a monolayer of gold-silica core-shell nanoparticles is formed first, and the resultant nanoparticle monolayer is deposited onto chemically modified various solid substrates. Then, the silica shells of the nanoparticle monolayer are etched selectively to obtain nanogap structures of ultrasmall void. In addition, the nanogap structures are used to sense and analyze analytes.

In this experiment, the morphology of nanoparticles is measured by FESEM (field-emission scanning electron microscope) [SIGMA SEM available from Carl Zeiss, accelerated voltage 2.00 kV] and EFTEM (energy-filtered transmission electron microscopy) [LIBRA 120 microscope available from Carl Zeiss, accelerated voltage 120 kV]. Meanwhile, UV-Vis absorbance spectra for measuring reflectance spectra are obtained by using JASCO V530 spectrophotometer.

Hereinafter, each step of an embodiment of the present disclosure will be explained in more detail.

1. Preparation of Gold-Silica Core-Shell Nanoparticle Monolayer on Liquid Interface FIG. 1 is a schematic view illustrating a process for forming large-area uniform nanogap structures by transferring a monolayer of gold-silica core-shell nanoparticle monolayer self-assembled at air/liquid interface to various substrates and removing the silica shells through chemical etching in an Example of the present invention. FIG. 2 is a view illustrating the Raman enhancement effect of a nanogap structure formed by an ultrasmall void between metal cores after the etching of a shell.

First, gold-silica core-shell nanoparticles are prepared according to the known method (Non-patent Document 2) and used. That is, surfaces of citrate-stabilized gold nanoparticles are substituted with aminopropyltrimethoxysilane (APTMS) which is a silane coupling agent to modify the particle surfaces and then the particle surfaces are coated with silica shells through a condensation between the substituents and TEOS (tetraethylorthosilicate) which is a silica precursor. Two types of particles having a shell thickness of 5 nm and 2.5 nm are prepared as described below.

The gold-silica core-shell nanoparticles are subjected to a self-assembly at a liquid/liquid interface to obtain a monolayer of nanoparticles. That is, aqueous colloid (9 mL) of the gold-silica core-shell nanoparticles is poured into a plastic cup. Next, n-Hexane (3 mL) is added gradually to the top portion to form a liquid/liquid interface. Then, ethanol (4.5 mL) is introduced rapidly to the resultant colloid solution so that the core-shell nanoparticles are trapped at the hexane/water interface. After that, while hexane evaporates immediately, the trapped core-shell nanoparticles are self-assembled to form a highly close-packed monolayer over a large area.

For reference, the charged nanoparticles reduce the surface charge density thereof so that they may be adsorbed preferentially to the water/hexane interface.

Meanwhile, as for a Comparative Example, gold nanoparticles stabilized with citrate in aqueous solution without shell coating are subjected to the same procedure as the above Example to obtain a monolayer thin film of gold nanoparticles.

FIG. 3 is a view illustrating the characteristics of the gold-core silica-shell nanoparticles (Au@$SiO_2$ nanoparticles) (Example) and gold nanoparticles (Comparative Example) and the self-assembly of the particles at an air/water interface in an Example of the present invention and Comparative Example.

Figure 3A:
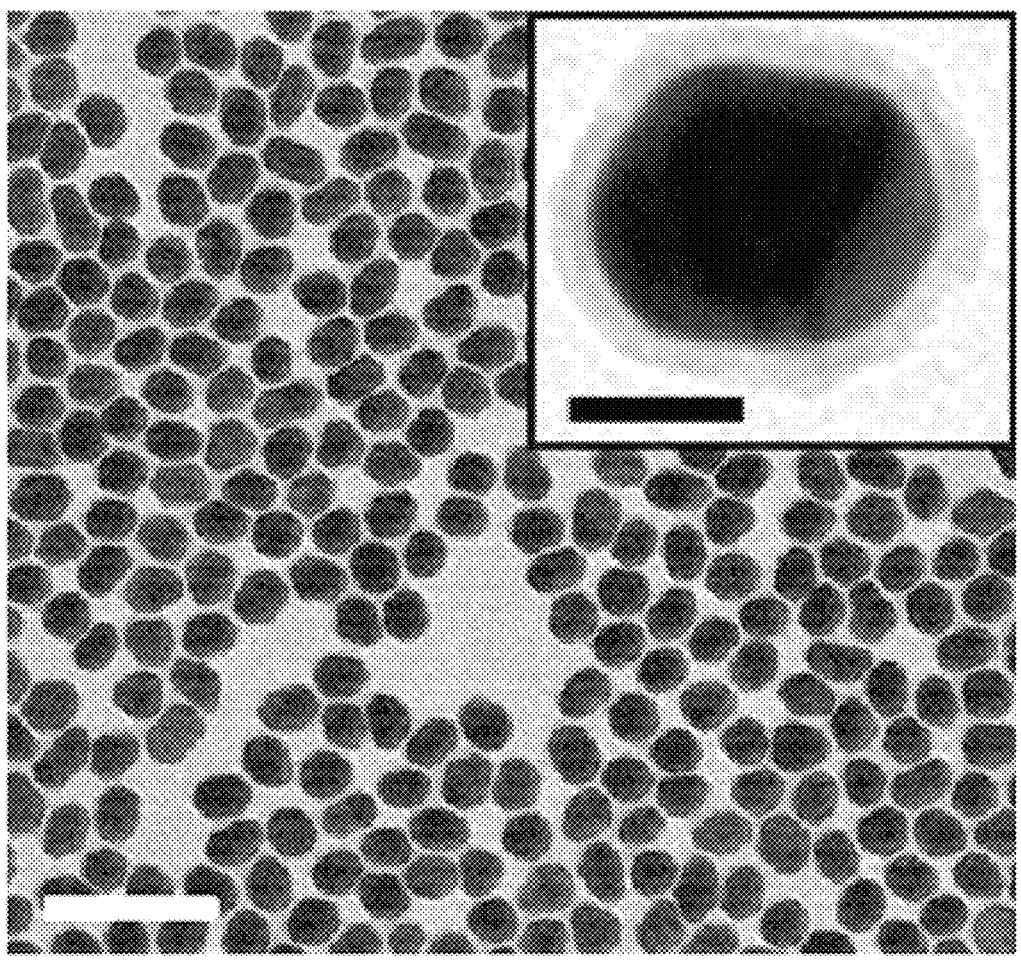
FIG. 3A is an energy-filtered transmission electron microscopic (EFTEM) image of gold-core silica-shell nanoparticles (Au@$SiO_2$ nanoparticles)

Particularly, FIG. 3A is an energy-filtered transmission electron microscopic (EFTEM) image of gold-core silica-shell nanoparticles (Au@$SiO_2$ nanoparticles), wherein the scale bar corresponds to 0.2 μm. In addition, the inset image is a magnification-enlarged image and the scale bar in the inset image corresponds to 20 nm.

Figure 3B:
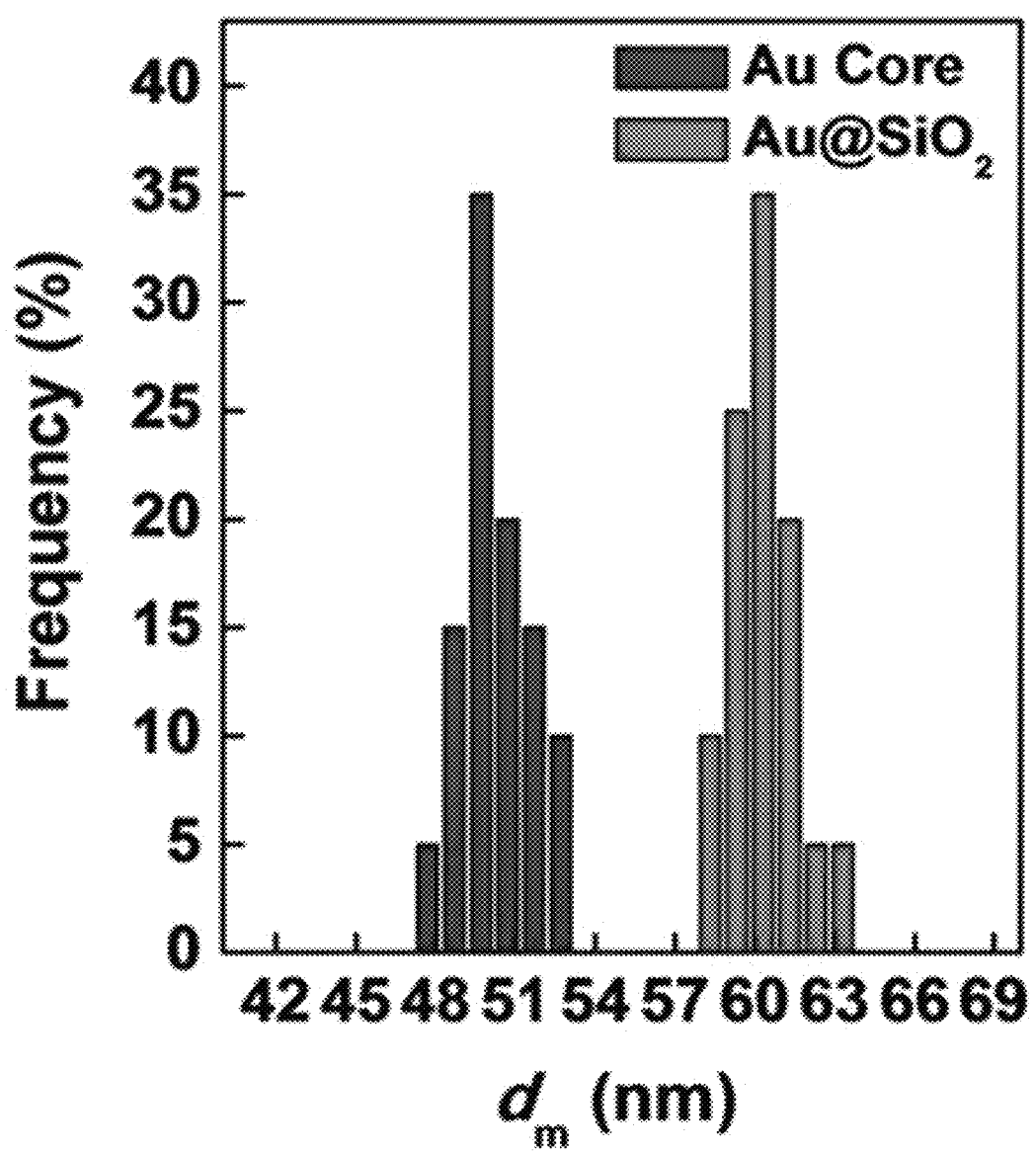
FIG. 3B shows a graph illustrating a size distribution (black colored graph) of gold (Au) cores (gold nanoparticles) and a size distribution (gray colored graph) of gold-core silica-shell nanoparticles (Au@$SiO_2$ nanoparticles)

FIG. 3B shows a graph illustrating a size distribution (black colored graph) of gold (Au) cores (gold nanoparticles) and a size distribution (gray colored graph) of gold-core silica-shell nanoparticles (Au@$SiO_2$ nanoparticles).

It can be seen from the graph that since the gold-core silica-shell nanoparticles (Au@$SiO_2$ nanoparticles) have an average diameter of about 60±1.3 nm and the size distribution of gold cores themselves is about 50±1.3 nm, the silica shell has a thickness of about 5 nm.

Figure 3C:
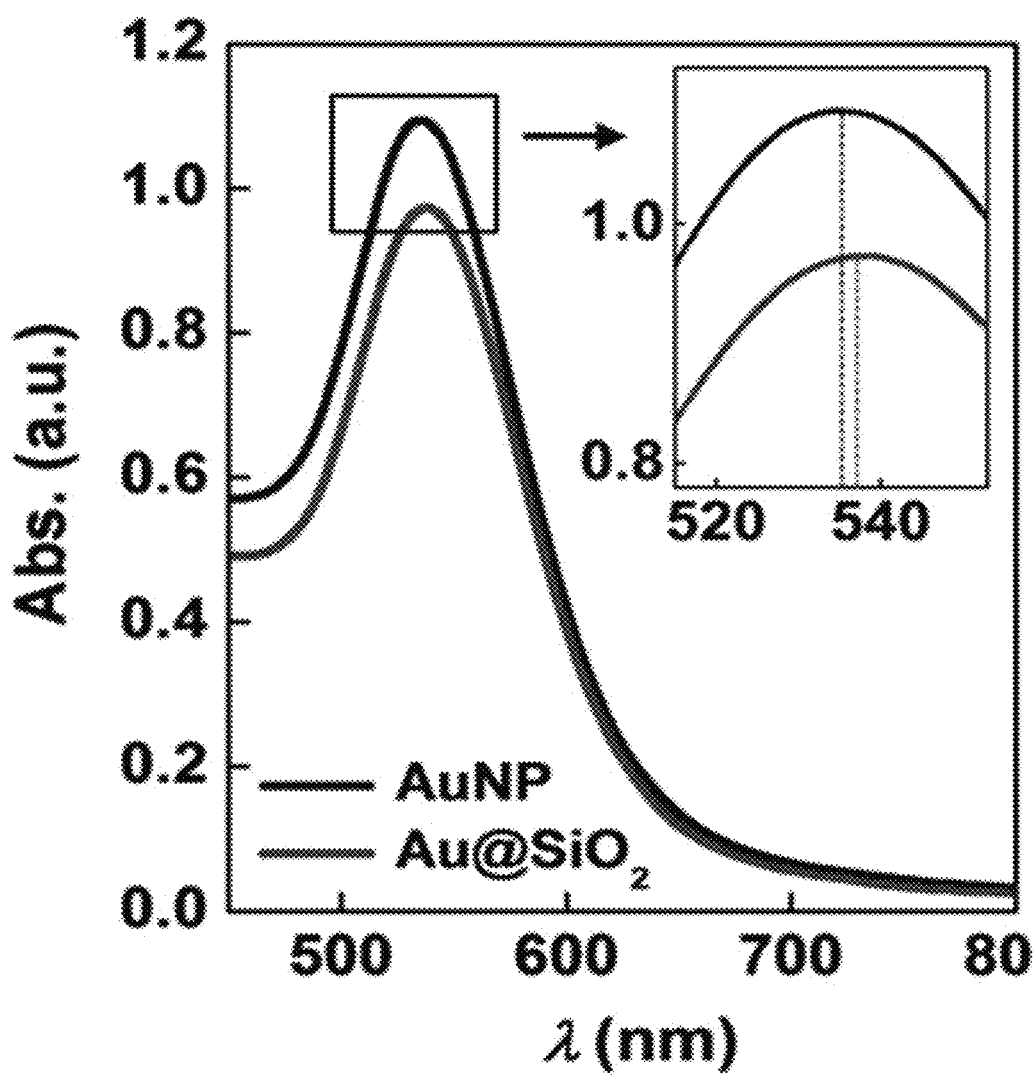
FIG. 3C shows an absorbance spectra (lower side gray colored graph) of a solution of gold-core silica-shell nanoparticles (Au@$SiO_2$ nanoparticles) and an absorbance spectra (upper side black colored graph) of gold nanoparticles having no shells.

FIG. 3C shows an absorbance spectra (lower side gray colored graph) of a solution of gold-core silica-shell nanoparticles (Au@$SiO_2$ nanoparticles) and an absorbance spectra (upper side black colored graph) of gold nanoparticles per se.

Since the silica shell has a higher refractive index as compared to water, the surface plasmonic resonance (SPR) band undergone a slight red-shift from 535 nm to 539 nm. This can be also seen from FIG. 4A (in case of a shell thickness of 2.5 nm).

Figure 3D:
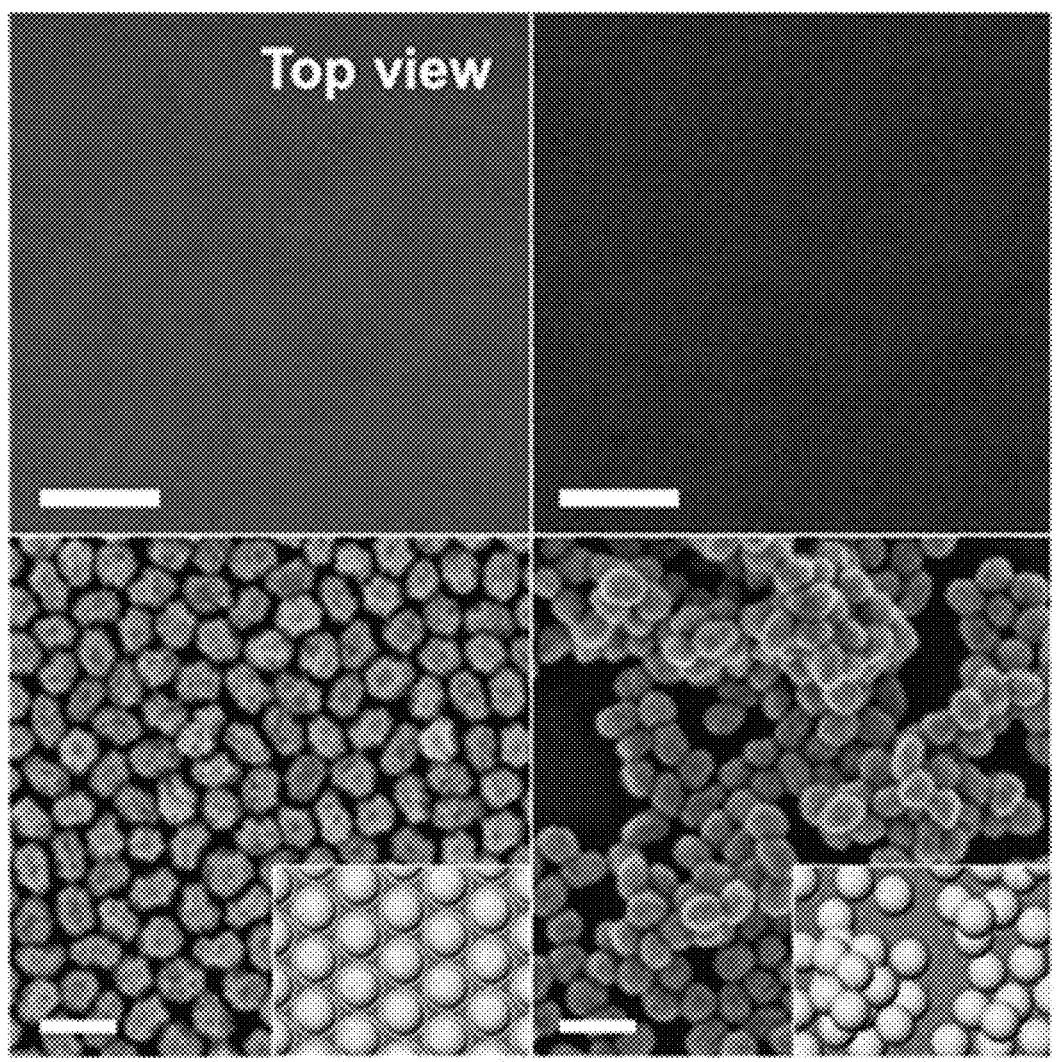
FIG. 3D shows a photographic image (left side upper image) and FESEM image (left side lower image) of gold-core silica-shell nanoparticles (Au@$SiO_2$ nanoparticles) self-assembled at an air/water interface and a photographic image (right side upper image) and FESEM image (right side lower image) of gold nanoparticles having no shells.

FIG. 3D shows a photographic image (left side upper image) and FESEM image (left side lower image) after transferred to a glass of gold-core silica-shell nanoparticles (Au@$SiO_2$ nanoparticles) [Example] self-assembled at an air/water interface and a photographic image (right side upper image) and FESEM image (right side lower image) after transferred to a glass of gold nanoparticles having no shells [Comparative Example]. As described above, having no shells herein refers to Comparative Example where gold nanoparticles having no shells from the beginning are used. Herein, the scale bars of the upper images correspond to 1.5 nm and those of the lower images correspond to 100 nm.

As can be seen from FIG. 3D, the contours of the gold-core silica-shell nanoparticles (Au@$SiO_2$ nanoparticles) assembled at an air/water interface are significantly lighter as compared to the gold nanoparticles having no shells.

In addition, after comparing the self-assembled shape of the nanoparticles having silica shells with that of the nanoparticles having no shells, it can be seen that the silica shell coating allows a formation of a monolayer of uniform nanoparticles. Therefore, it can be seen that such shell coating helps the formation of a monolayer of uniform nanoparticles without particle aggregation.

Figure 4A:
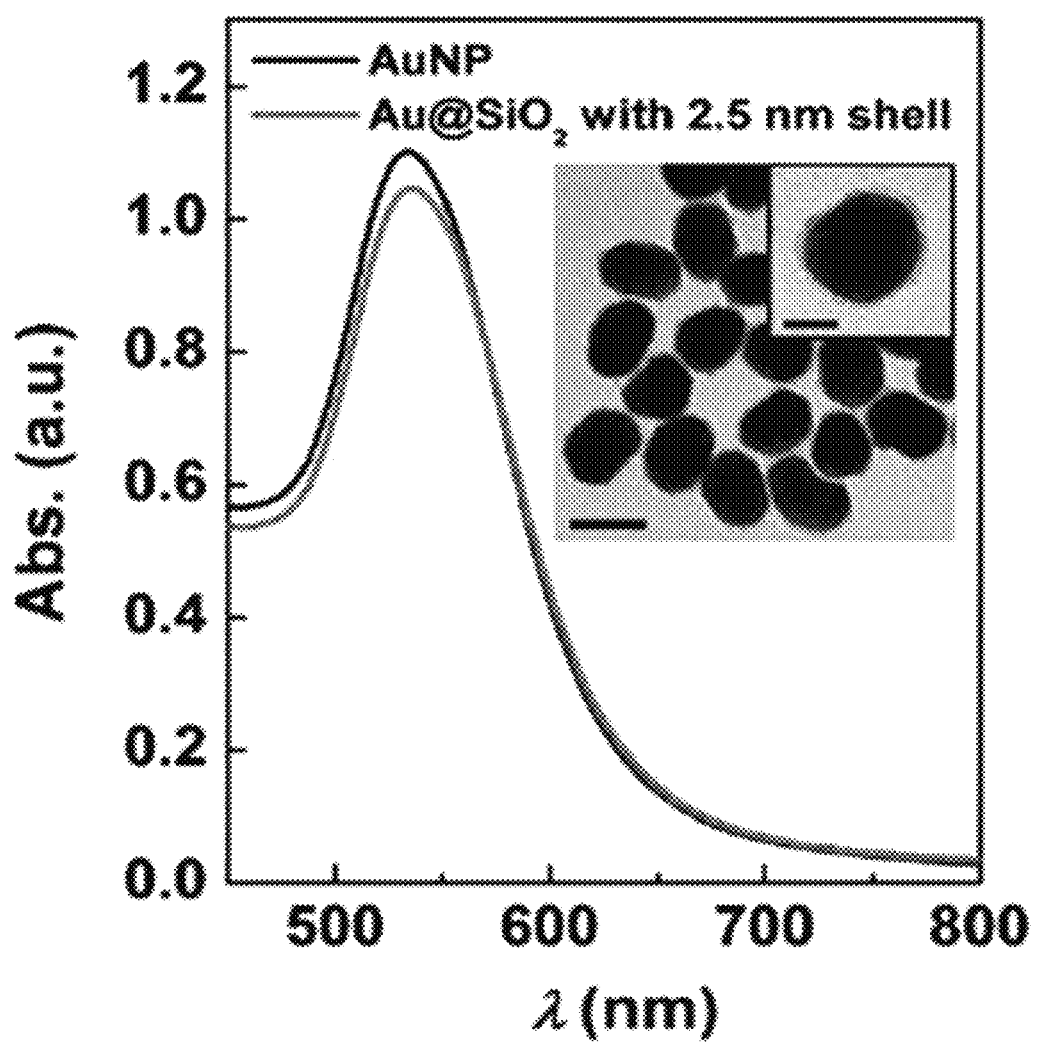
FIG. 4A shows a UV-Vis absorbance spectra of gold-core silica-shell nanoparticles (Au@$SiO_2$ nanoparticles) having a shell thickness of 2.5 nm and a UV-Vis absorbance spectra of gold nanoparticles in an example.

Meanwhile, FIG. 4A shows a UV-Vis absorbance spectra of gold nanoparticles and a UV-Vis absorbance spectra of gold-core silica-shell nanoparticles (Au@$SiO_2$ nanoparticles) having a shell thickness of 2.5 nm. In FIG. 4A, the scale bar of the EFTEM image in the graph corresponds to 50 nm and the inset FETEM image in the corresponding image is an enlarged image. The scale bar of the inset FETEM image corresponds to 20 nm.

Figure 4B:
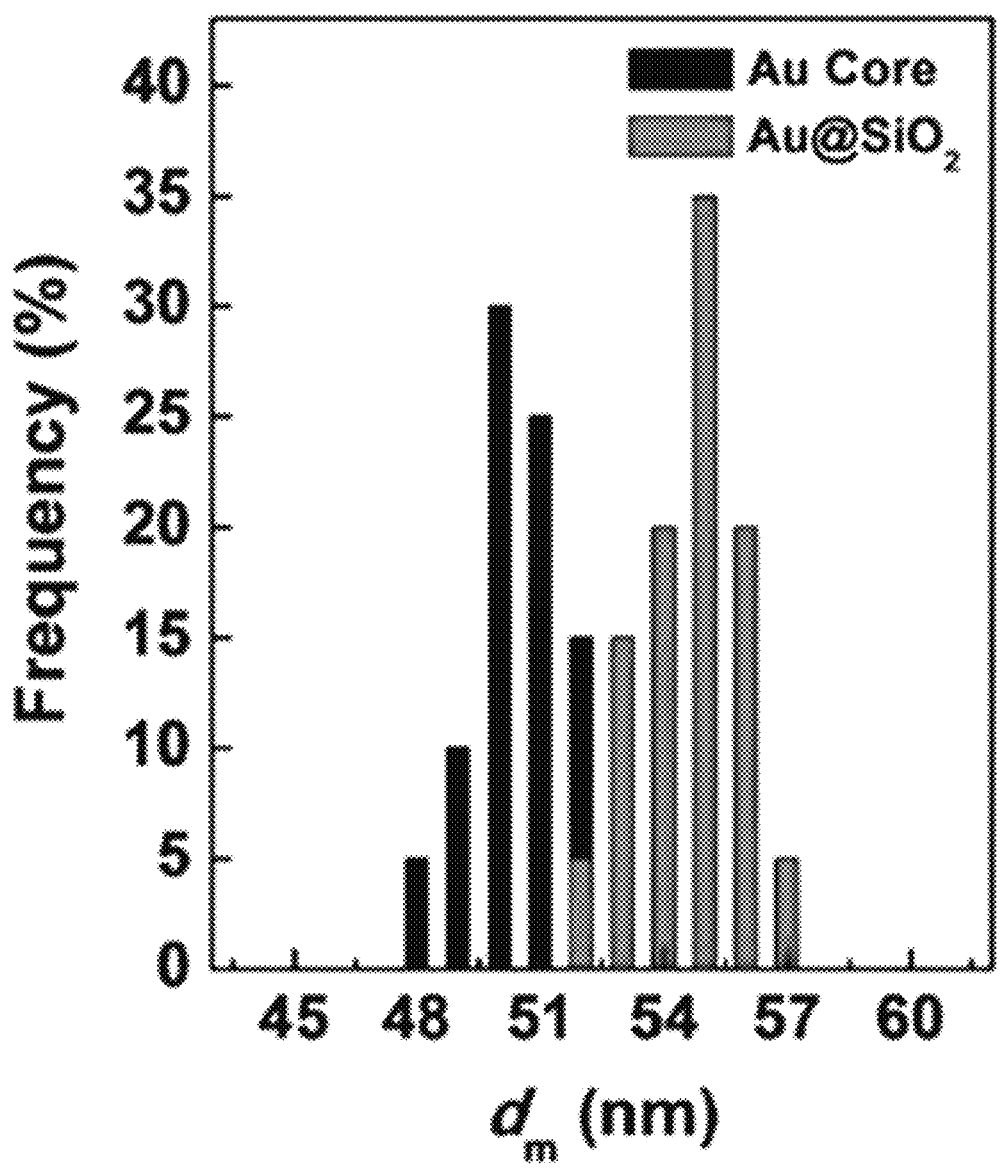
FIG. 4B is a graph illustrating a size distribution (black) of Au cores [Comparative Example] and a size distribution (gray) of gold-core silica-shell nanoparticles (Au@$SiO_2$ nanoparticles) [Example having a shell thickness of 2.5 nm]

FIG. 4B is a graph illustrating a size distribution (black) of Au cores and a size distribution (gray) of gold-core silica-shell nanoparticles (Au@SiO$_2$ nanoparticles). It can be seen that since the gold-core silica-shell nanoparticles (Au@SiO$_2$ nanoparticles) have an average diameter of about 55±1.3 nm and the size distribution of gold cores themselves is about 50±1.3 nm, the silica shell has a thickness of about 2.5 nm.

2. Preparation of Monolayer of Gold-Silica Core-Shell Nanoparticles Transferred to Various Solid Substrates To transfer a monolayer of gold-silica core-shell nanoparticles onto a solid substrate, various substrates (polymer substrate, glass substrate, or the like) (1 cm×1 cm, 1 nm thickness) are prepared and surface-modified.

To increase the adhesion between the substrate surface and the surface of metal-silica core-shell nanoparticles, a PDMS substrate having more adhesive surface is prepared. Particularly, Sylgard 184 (available from Dow Corning) elastomer is mixed with a curing agent (mixing ratio: 25:1 w/w) and degassed under vacuum for about 15 minutes, and then air bubbles are removed from PDMS. The resultant mixture is cured in an oven at 65° C. for 12 hours.

In addition, the glass substrate and ITO (indium tin oxide) substrate are modified with APTSM (3-aminopropyltrimethoxysilane) and treated with OTS (octadecyltrichlorosilane) to provide substrates having reduced hydrophilicity and improved binding force with the core-shell nanoparticles.

Particularly, the glass substrate and ITO slide are cleaned with a piranha solution (H$_2$SO$_4$/H$_2$O$_2$=7:3 v/v) for 30 minutes and washed with deionized water, followed by drying under nitrogen. The washed slide is dipped in an ethanol solution containing APTMS (3-aminopropyltrimethoxysilane, 5% v/v) to carry out aminosilylation. After the APTMS treatment, the slide is washed with ethanol and deionized water and dried under nitrogen, and then treated with OTS (octadecyltrichlorosilane, 5 mM) in a toluene solution in order to impart surface hydrophobocity. For reference, since it is difficult to transfer a monolayer of nanoparticles to a glass substrate, etc. due to hydrophilic characteristics, the substrate is treated to reduce such hydrophilic characteristics. Then, the substrate is washed with ethanol and deionized water to remove the compounds remaining on the surface, followed by drying under nitrogen.

With regard to the transfer, the monolayer is transferred to a substrate by bringing the substrate in parallel with the water surface and then touching therewith lightly.

FIG. 5 is a view illustrating the characteristics of a monolayer of gold-core silica-shell nanoparticles ((Au@SiO$_2$ nanoparticles) after it is transferred to solid substrates in an example of the present invention. The scale bars of the images of FIG. 5 correspond to 15 mm.

Figure 5A:
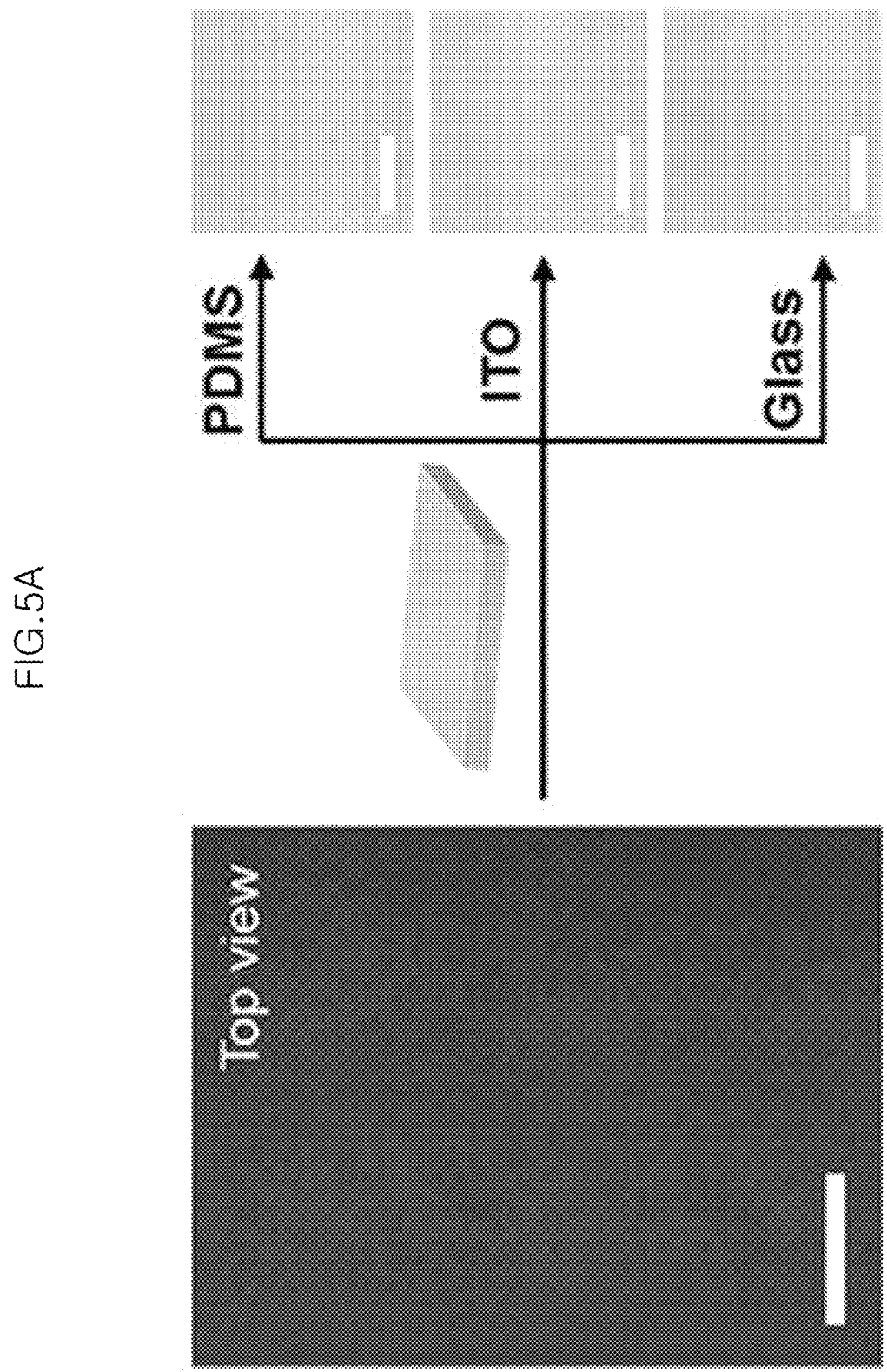
FIG. 5A shows a photograph (left-side) of the monolayer of gold-core silica-shell nanoparticles (Au@$SiO_2$ nanoparticles) self-assembled at an air/water interface, and the right-side images are photographs of the monolayer after being transferred to PDMS, ITO glass and glass, as viewed from the top to the bottom, respectively, in an example.

Particularly, FIG. 5A shows a photograph (left-side) of the monolayer of gold-core silica-shell nanoparticles (Au@SiO$_2$ nanoparticles) self-assembled at an air/water interface, and the right-side images are photographs of the monolayer after being transferred to PDMS, ITO glass and glass, each as viewed sequentially from the top.

Figure 5B:
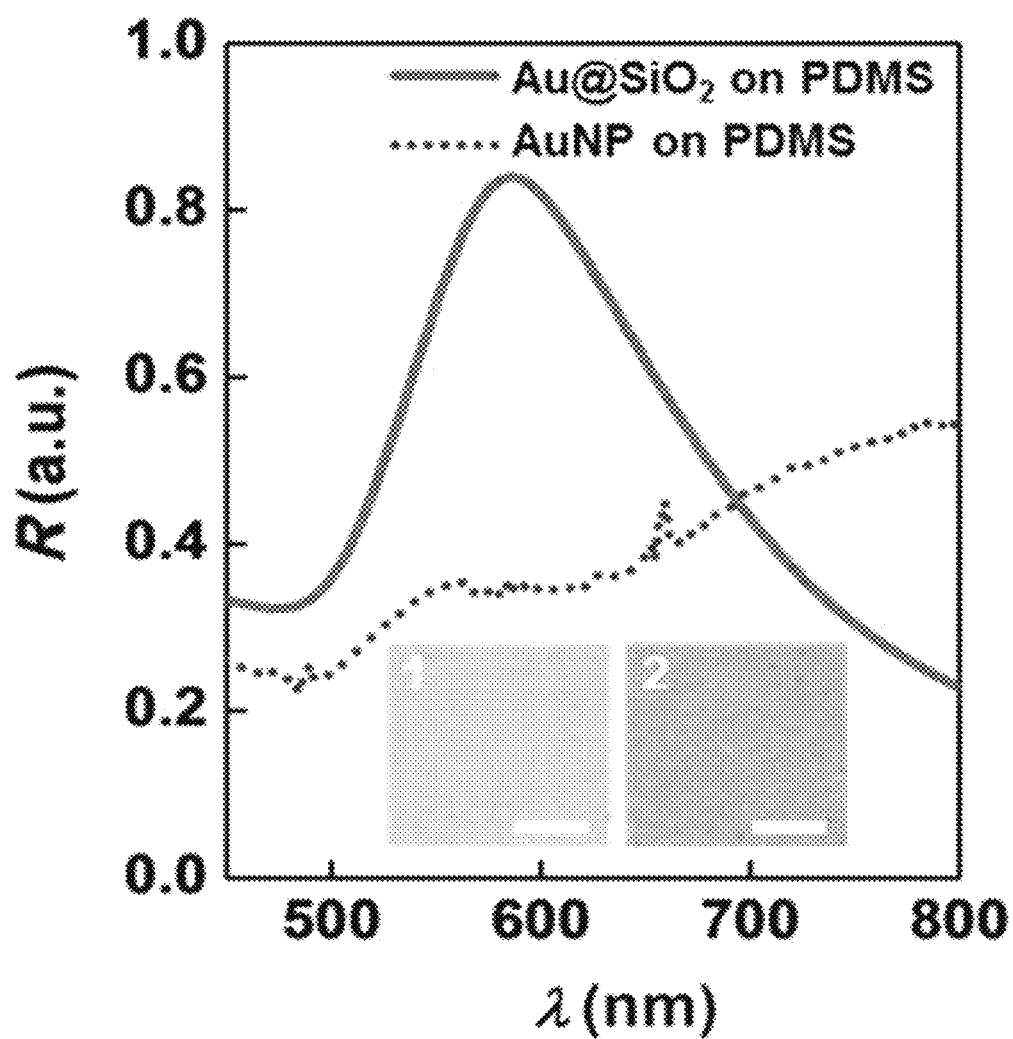
FIG. 5B shows a photograph (No. 1) and a graph (solid line) of reflectance spectra of the monolayer of gold-core silica-shell nanoparticles (Au@$SiO_2$ nanoparticles) after being transferred to a PDMS substrate and a photograph (No. 2) and a graph (dotted line) of reflectance spectra of the layer of citrate-stabilized Au nanoparticles after being transferred to a PDMS substrate, in an example.

FIG. 5B shows a photograph (No. 1) and a graph (solid line) of reflectance spectra of the monolayer of gold-core silica-shell nanoparticles (Au@SiO$_2$ nanoparticles) after being transferred to a PDMS substrate and a photograph (No. 2) and a graph (dotted line) of reflectance spectra of the layer of citrate-stabilized Au nanoparticles having no shells after being transferred to a PDMS substrate. Herein, having no shells refers to that gold nanoparticles having no shells from the beginning are used.

As can be seen from FIG. 5B, the reflective index of the monolayer of gold-core silica-shell nanoparticles (Au@SiO$_2$ nanoparticles) transferred to a PDMS substrate shows a clear SPR band at around 590 nm, which shows a red-shift by 51.0 nm as compared to the gold-core silica-shell nanoparticles (Au@SiO$_2$ nanoparticles) which are colloidal in water. Such a shift is caused by a change in dielectric environment (i.e. change from air/water to air/PDMS) and a decrease in interparticle distance of the adjacent gold-core silica-shell nanoparticles (Au@SiO$_2$ nanoparticles).

Meanwhile, a single SPR band is observed from the monolayer of the gold-core silica-shell nanoparticles (Au@SiO$_2$ nanoparticles) on PDMS due to the silica shell between nanoparticles. On the contrary, the gold core particles transferred to the same substrate show a wide range of reflectivity over a large spectral region, which suggests formation of randomly aggregated nanoparticles.

Figure 5C:
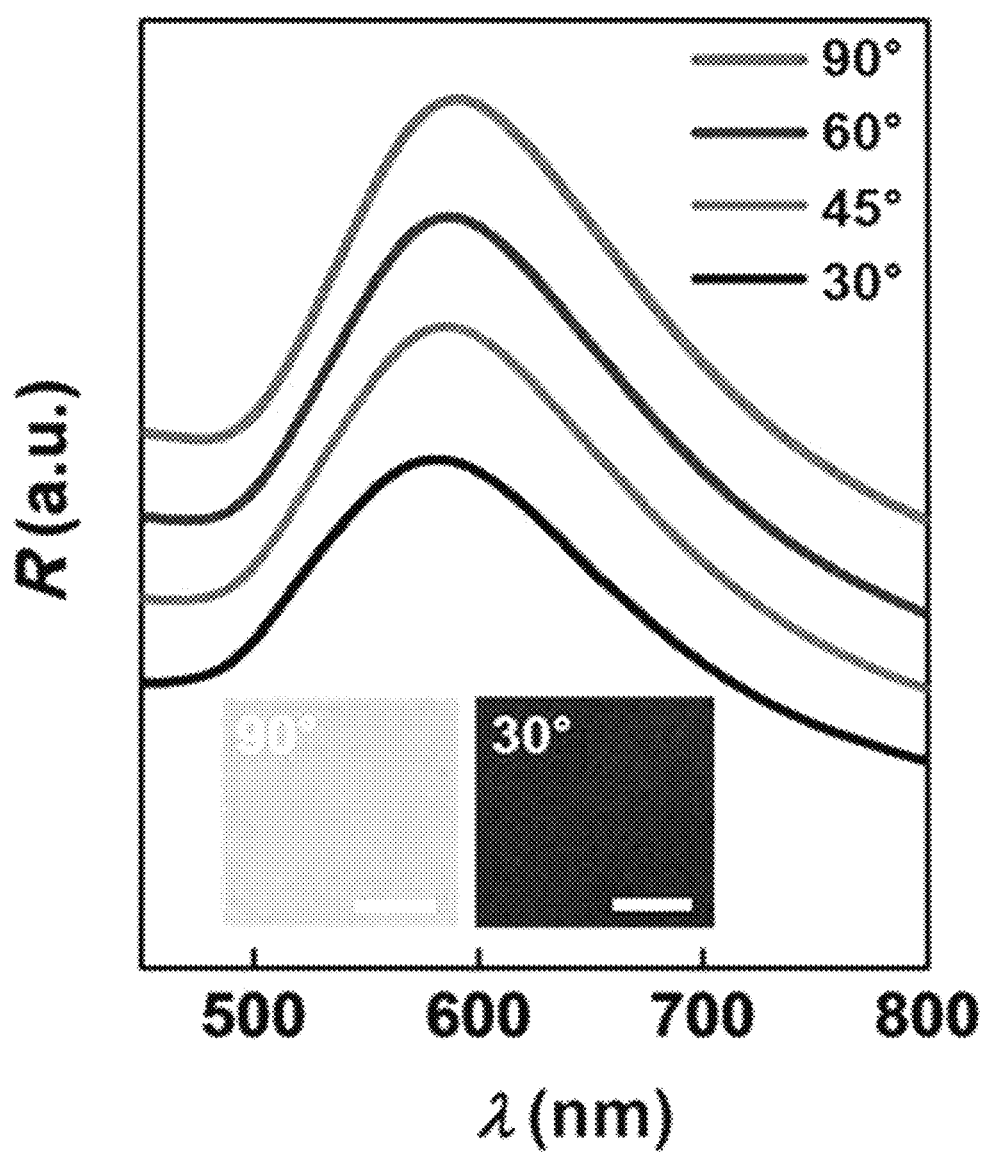
FIG. 5C shows a photograph (at 90° and 30°) of the monolayer of gold-core silica-shell nanoparticles (Au@$SiO_2$ nanoparticles) after being transferred to a PDMS substrate depending on incidence angle and a graph of reflectance spectra (at an incidence angle of 90°, 60°, 45° and 30° from the top sequentially), in an example.

FIG. 5C shows a photograph (at 90° and 30°) of the monolayer of gold-core silica-shell nanoparticles (Au@SiO$_2$ nanoparticles) after being transferred to a PDMS substrate depending on incidence angle and a graph of reflectance spectra (at an incidence angle of 90°, 60°, 45° and 30° from the top sequentially). Herein, incidence angle refers to an angle of incident light to the normal direction to the substrate surface to which the monolayer is transferred. The angle of the incident light input in the normal direction to the substrate is 90°, and an incidence angle of 30° is the angle of the incident light changed from the normal direction to the substrate surface.

The monolayer of gold-core silica-shell nanoparticles (Au@SiO$_2$ nanoparticles) transferred to a PDMS substrate shows two characteristic scattering colors depending on incident angle. The reflected color shows a yellow color at the incident angle, i.e., normal angle of the incident light, and is changed into a blue color as the incident angle is decreased from 90° to 30°.

Meanwhile, after checking the reflectance spectra depending on incident angle, the reflectance spectra of the monolayer of gold-core silica-shell nanoparticles (Au@SiO$_2$ nanoparticles) undergoes a slight shift from 591 nm to 582 nm, as the incident angle is changed from 90° to 30°.

3. Preparation of Ultrasmall Void Metallic Nanogap Structures on Various Solid Substrates The monolayer of gold-silica core-shell nanoparticles is dipped in a sodium hydroxide solution (NaOH, 5M) to carry out chemical etching of the silica shells surrounding the gold core nanoparticles. After the etching, the monolayer is washed with water to remove undesired reactants on the solid substrate and then the remaining water is removed immediately under nitrogen gas.

Different etching times (i.e., 15 minutes, 30 minutes, 60 minutes, 90 minutes, 120 minutes, and 150 minutes) are used to determine a decrease in interparticle distance between gold core nanoparticles depending on time. It is thought that such a phenomenon is caused by Van der Waals interaction between negatively charged gold nanoparticles due to a high cation concentration of NaOH solution. As a result, ultrasmall void nanogaps having a size of about 1-2 nm and having no limitation in diffusion between cores are obtained. This will be explained in more detail hereinafter.

FIG. 6A shows a schematic view and photograph (left-side) of the monolayer of gold-core silica-shell nanoparticles (Au@SiO$_2$ nanoparticles) having a shell thickness of 5.0 nm on PDMS, and a schematic view and photograph (right-side) of the layer of Au core particles in which the shells are etched after carrying out etching of the monolayer for 150 minutes, in an example of the present invention. Herein, the scale bar corresponds to 1.5 mm. The inset image in FIG. 6A is an image taken by FESEM, and the scale bar in the inset image corresponds to 50 nm.

The reflected color of the layer of gold-core silica-shell nanoparticles (Au@SiO$_2$ nanoparticles) is changed slightly from yellow to brown-yellow. In addition, interestingly, the distance between gold cores is decreased from 10 nm to about 1-2 nm, as can be seen from the FESEM image.

To examine the etching ratio of silica shells in more detail, variations in silica shell of each of the particles after various etching times are visualized through EFTEM.

FIG. 6B is an EFTEM image illustrating a change in silica shell of each of gold-core silica-shell nanoparticles (Au@SiO$_2$ nanoparticles) after various etching times, in an example of the present invention. In FIG. 6B, the scale bar corresponds to 20 nm.

Figure 6C:
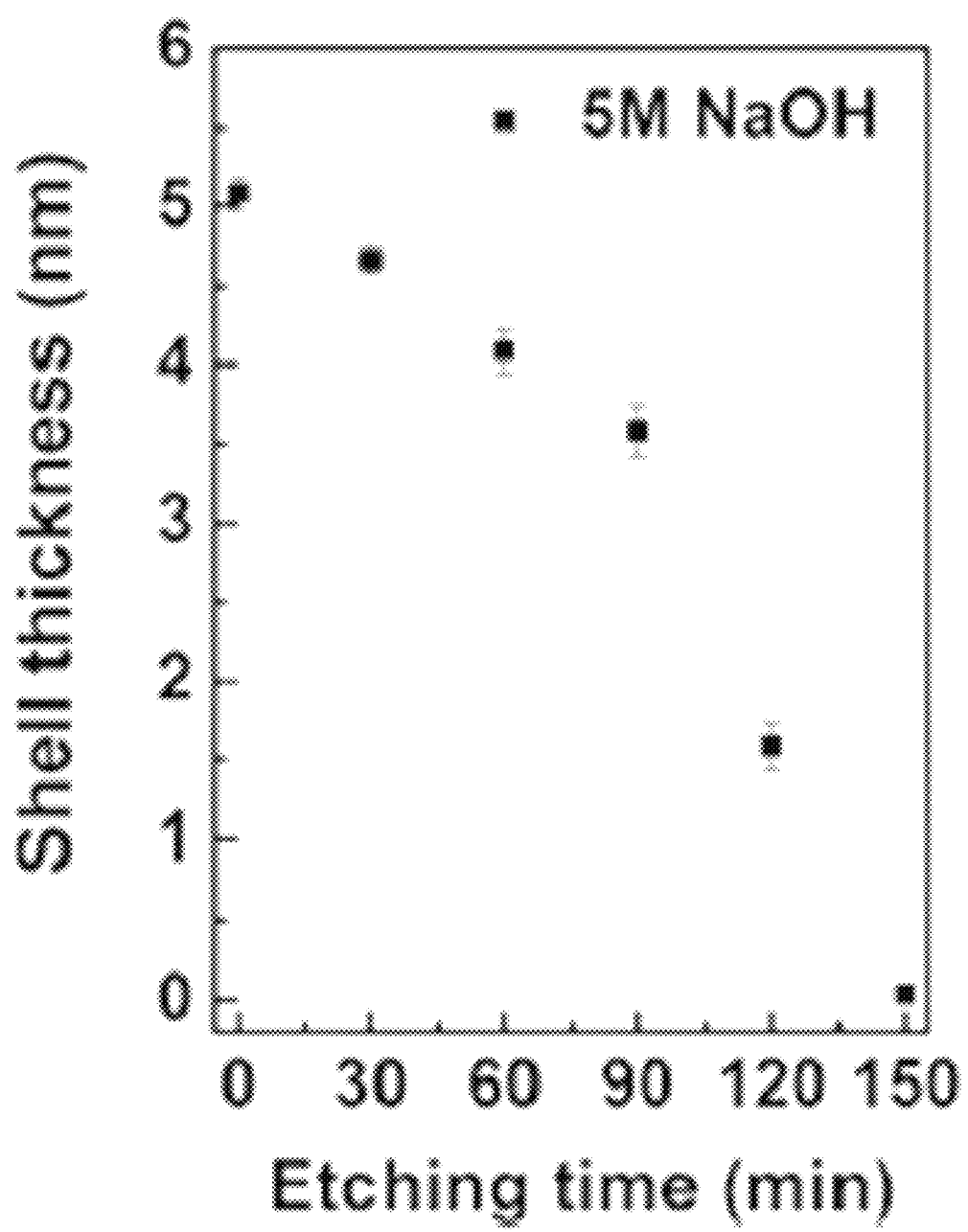
FIG. 6C is a graph illustrating a change of shell thickness depending on an increase in etching time which are measured from 20 particles in the EFTEM image.

FIG. 6C is a graph illustrating a change in shell thickness depending on an increase in etching time as measured from 20 particles in the EFTEM image.

As can be seen from the EFTEM results, each of the particles undergoes a decrease in silica thickness on a TEM grid and the silica layer is removed completely after etching for about 150 minutes. Such results are very similar to the results obtained from the reflectance analysis and FESEM images.

Figure 6D:
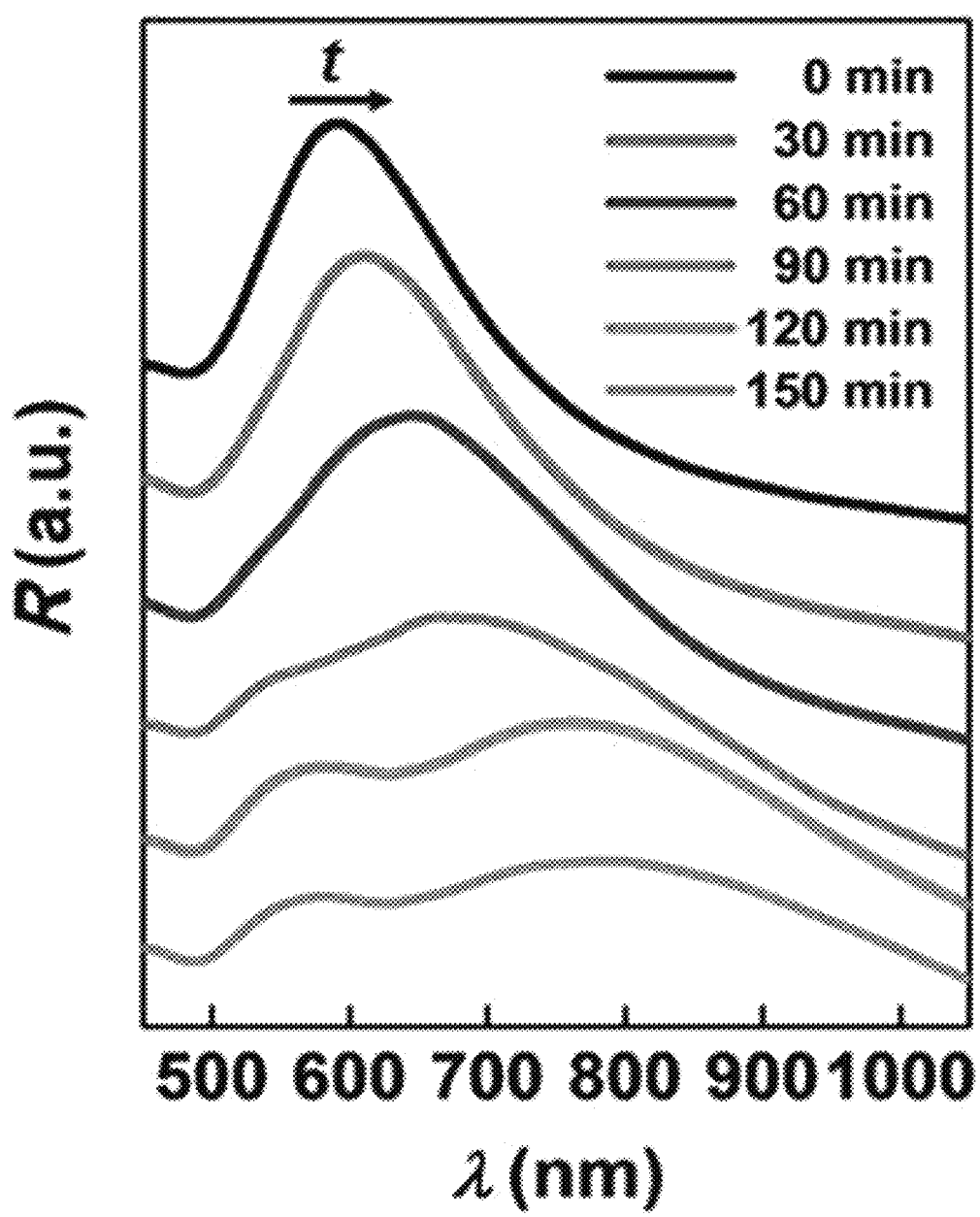
FIG. 6D is a reflectance spectra of the monolayer of gold-core silica-shell nanoparticles (Au@SiO$_2$ nanoparticles) on PDMS depending on chemical etching time in which graphs of 0 min., 30 min., 60 min., 90 min., 120 min., and 150 min. are viewed sequentially from the top.

FIG. 6D is a graph of reflectance spectra of the monolayer of gold-core silica-shell nanoparticles (Au@SiO$_2$ nanoparticles) on PDMS depending on chemical etching time of 0 min., 30 min., 60 min., 90 min., 120 min., and 150 min. as viewed sequentially from the top.

As can be seen from the graph, the single SPR band of the layer of gold-core silica-shell nanoparticles (Au@SiO$_2$ nanoparticles) undergoes a shift to provide two SPR bands at 581 nm and 786 nm with the lapse of reaction time. The same tendency is also observed in the layers of gold-core silica-shell nanoparticles (Au@SiO$_2$ nanoparticles) on an ITO substrate and on a glass substrate (see, FIG. 7).

Figure 6E:
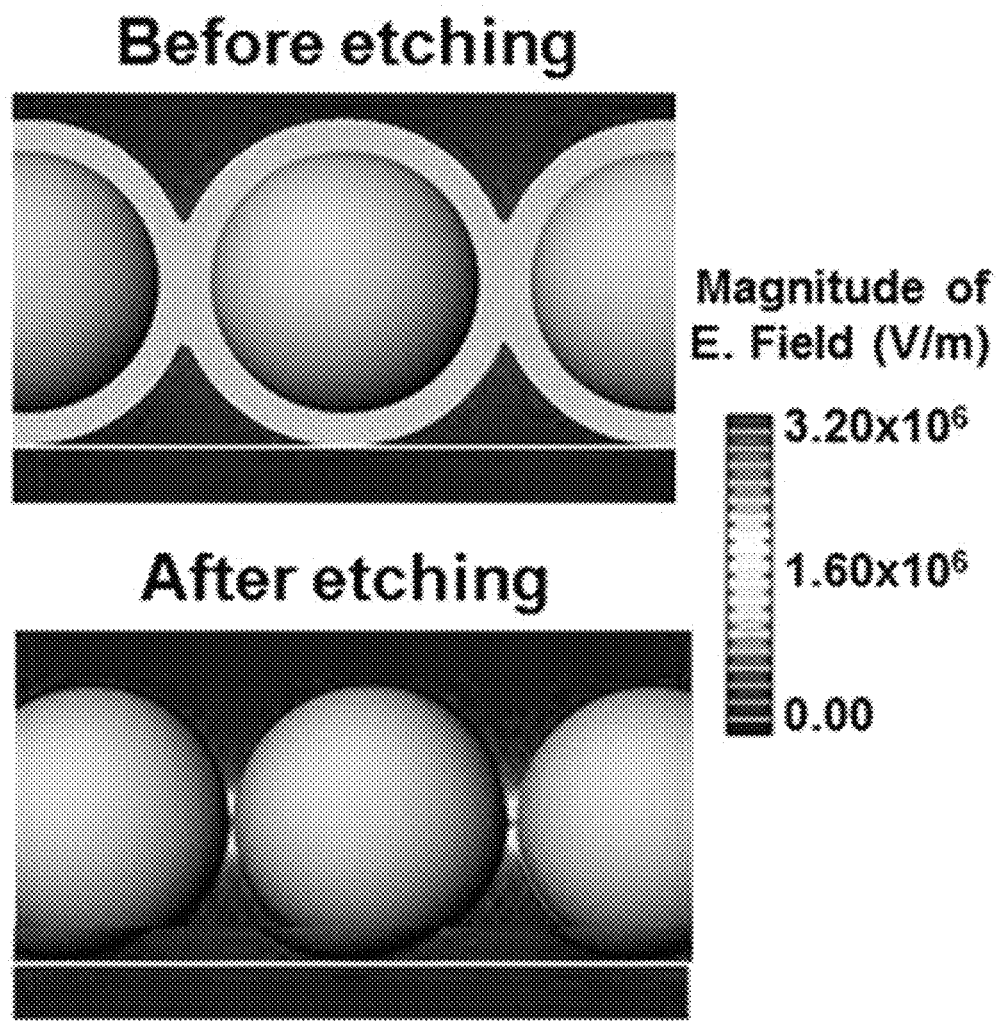
FIG. 6E is a photograph illustrating a decrease in intercore distance and electromagnetic field enhancement in the monolayer of gold-core silica-shell nanoparticles (Au@SiO$_2$ nanoparticles) before chemical etching (upper image) and after chemical etching (lower image)

FIG. 6E is a photograph illustrating a decrease in intercore distance and electromagnetic field enhancement in the monolayer of gold-core silica-shell nanoparticles (Au@SiO$_2$ nanoparticles) before chemical etching (upper image) and after chemical etching (lower image).

Figure 6F:
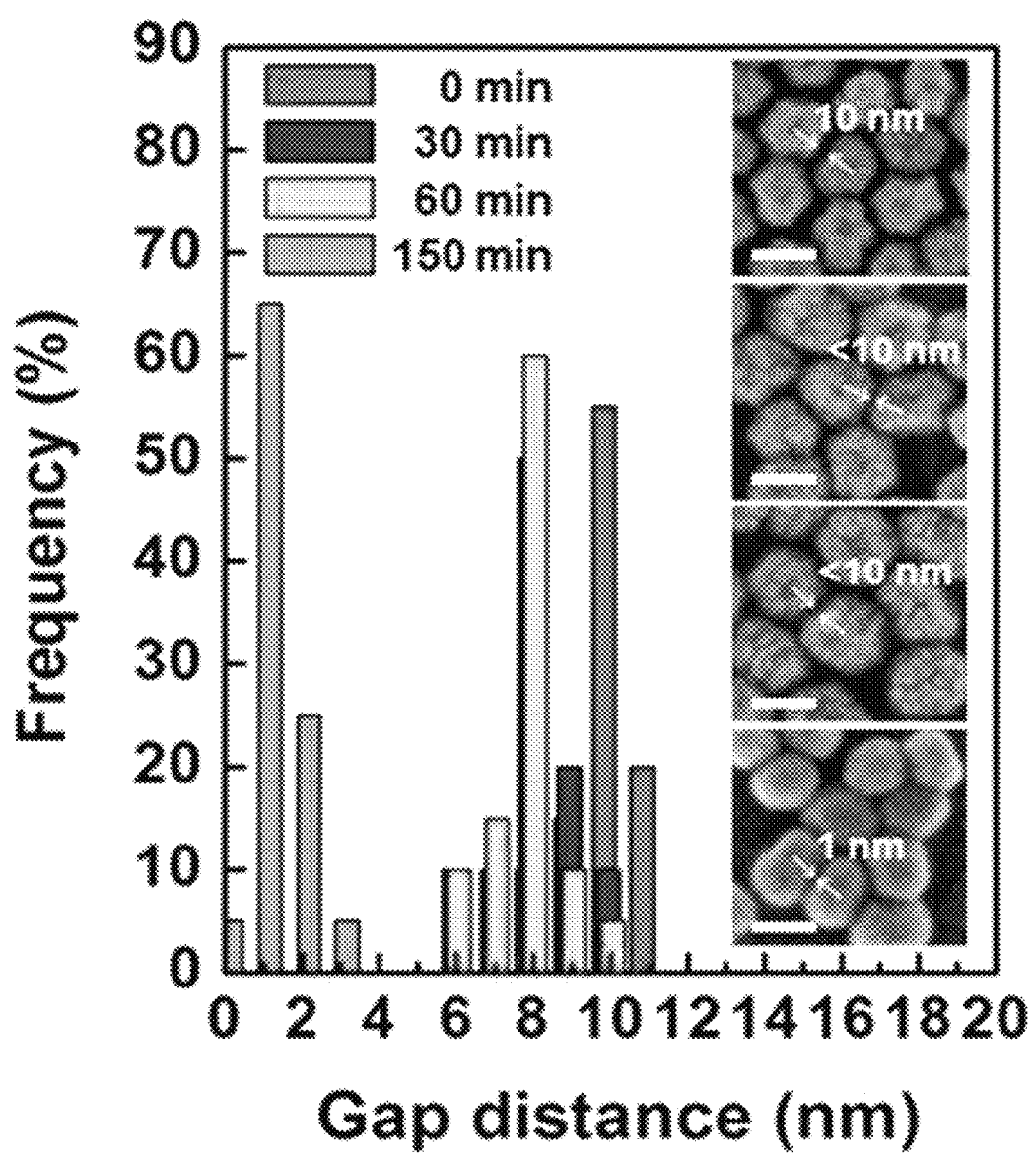
FIG. 6F and FIG. 6G show distribution diagrams of interparticle distance of Au cores in the monolayer of gold-core silica-shell nanoparticles (Au@SiO$_2$ nanoparticles) as a function of etching time.
Figure 6G:
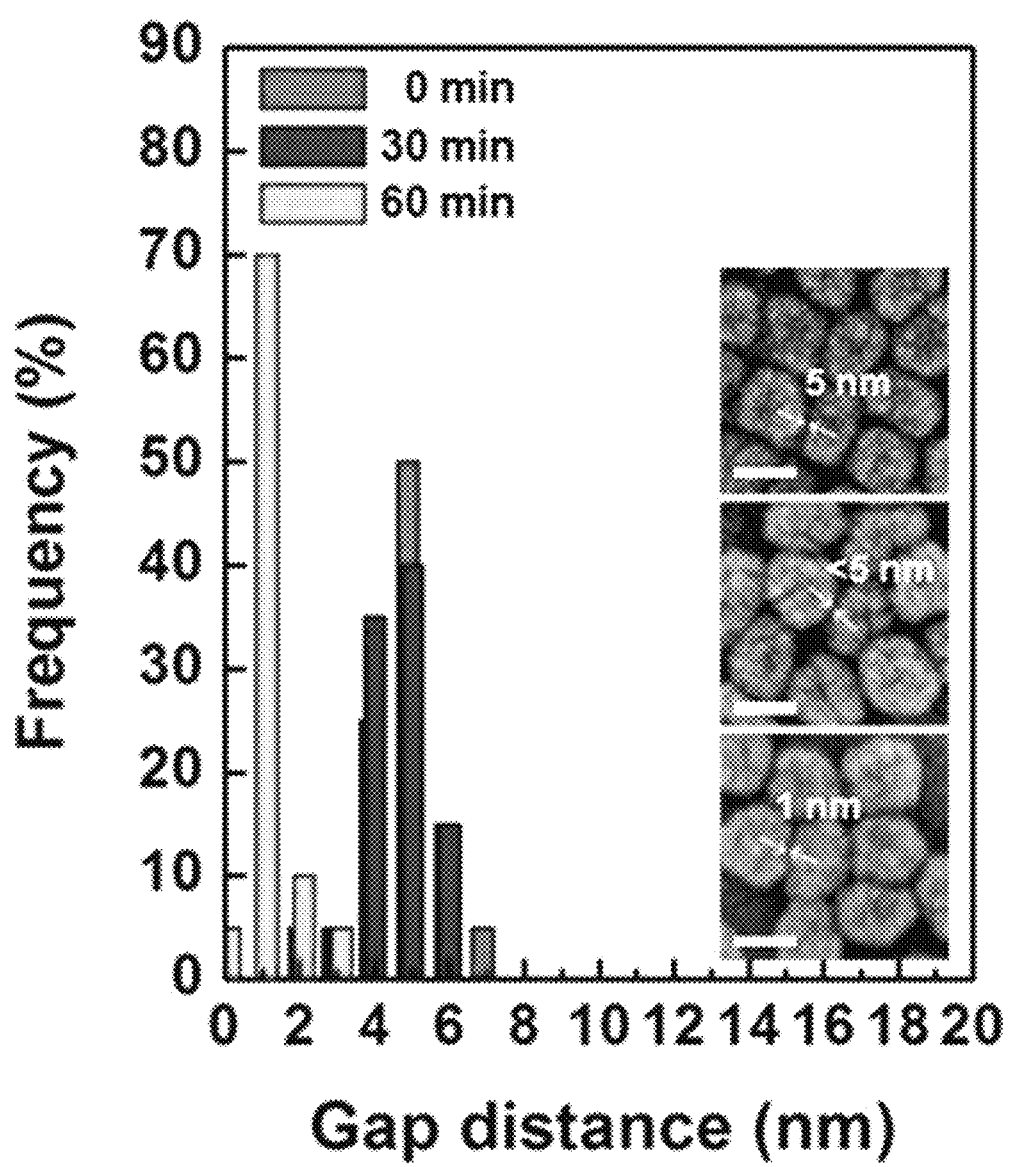

FIG. 6F and FIG. 6G show distribution diagrams of interparticle distance of Au cores in the monolayer of gold-core silica-shell nanoparticles (Au@SiO$_2$ nanoparticles) as a function of etching time. Herein, interparticle distance means the shortest distance between the adjacent particles. That is, it is determined by selecting 10 particles having 6 neighboring particles and measuring the shortest distance between gold cores with FESEM images.

More particularly, FIG. 6F and FIG. 6G shows the test results for the monolayers of gold/core silica/shell nanoparticles transferred to glass and having a silica shell with a different thickness. FIG. 6F corresponds to a silica shell having a thickness of 5.0 nm and FIG. 6G corresponds to a silica shell having a thickness of 2.5 nm. In FIG. 6F and FIG. 6G, gold cores have the same diameter of about 50 nm.

In FIG. 6F, it can be seen that the distance between gold cores are a spacing distance formed by the shell before etching (the shell thickness is about 5.0 nm, and thus the distance between gold cores is about 10 nm) but the distance becomes smaller than the spacing distance formed by the shell, after etching. The images in the graph of FIG. 6F show a decrease in intercore distance to 9.9±0.9 nm, 8.1±1.1 nm, 7.9±0.9 nm and 1.3±0.7 nm, as viewed from the top.

It can be also seen from FIG. 6G that the distance between gold cores are a spacing distance formed by the shell before etching (the shell thickness is about 2.5 nm, and the distance between gold cores is about 5 nm) but the distance becomes smaller than the spacing distance formed by the shell, after etching. The images in the graph of FIG. 6G show a decrease in intercore distance to 5.0±0.9 nm, 4.6±1.0 nm and 1.5±0.3 nm, as viewed from the top.

The reason why the interparticle distance is decreased after chemical etching may be said as follows.

That is, when the silica shells are removed from the layer of gold-core silica-shell nanoparticles (Au@SiO$_2$ nanoparticles) by a basic solution, electrostatic repulsive force is decreased significantly due to a high ion concentration. This induces Van der Waals attraction between particles so that the nanoparticles become closer with each other.

Figure 7A:
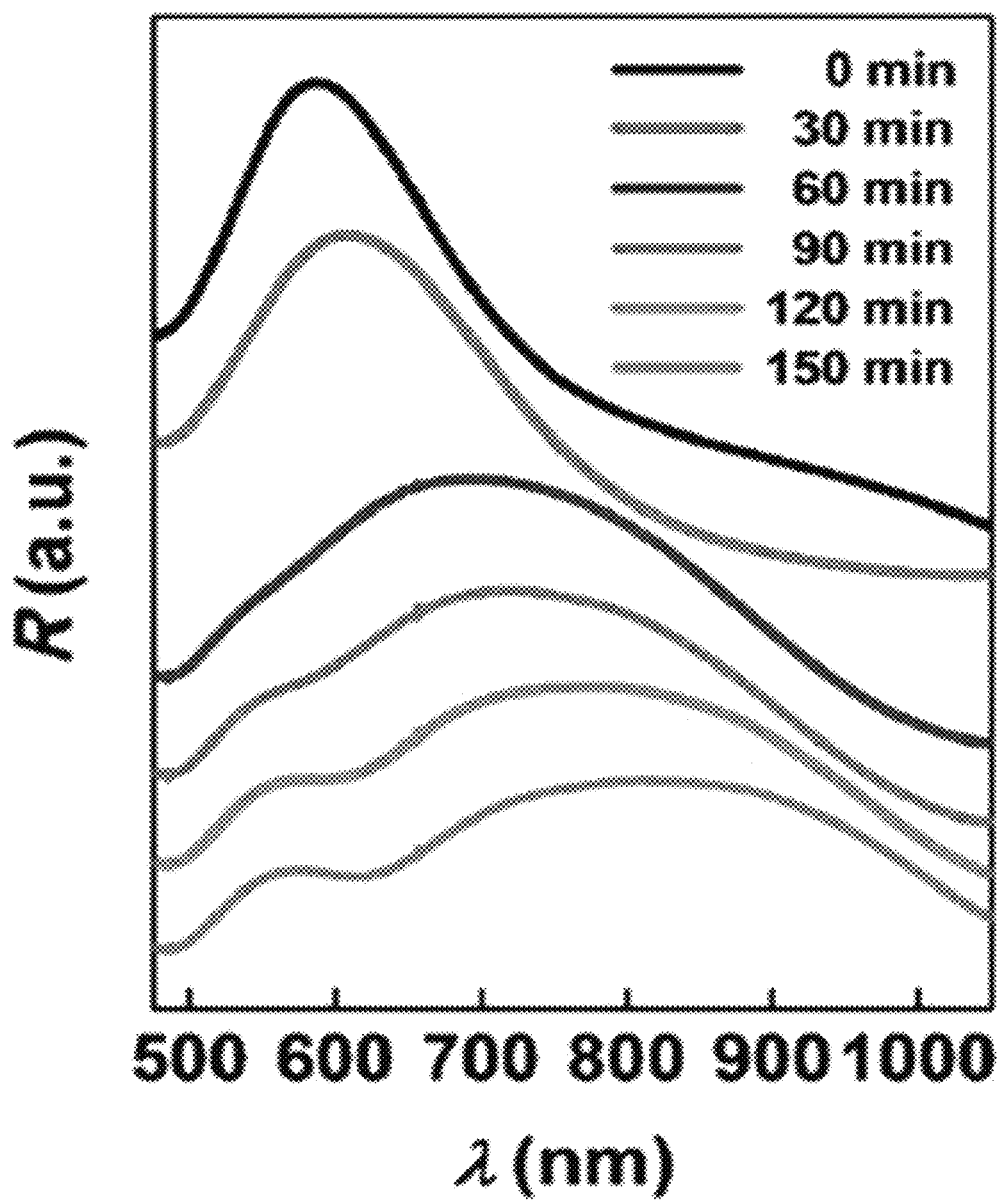
FIG. 7A and FIG. 7B show the reflectance spectra of the monolayer of gold-core silica-shell nanoparticles (Au@SiO$_2$ nanoparticles) having a silica shell with a thickness of 5.0 nm and transferred to an ITO substrate and glass substrate, respectively, as a function of etching time in an example, wherein in each figures, graphs of 0 min., 30 min., 60 min., 90 min., 120 min., and 150 min., are viewed sequentially from the top.
Figure 7B:
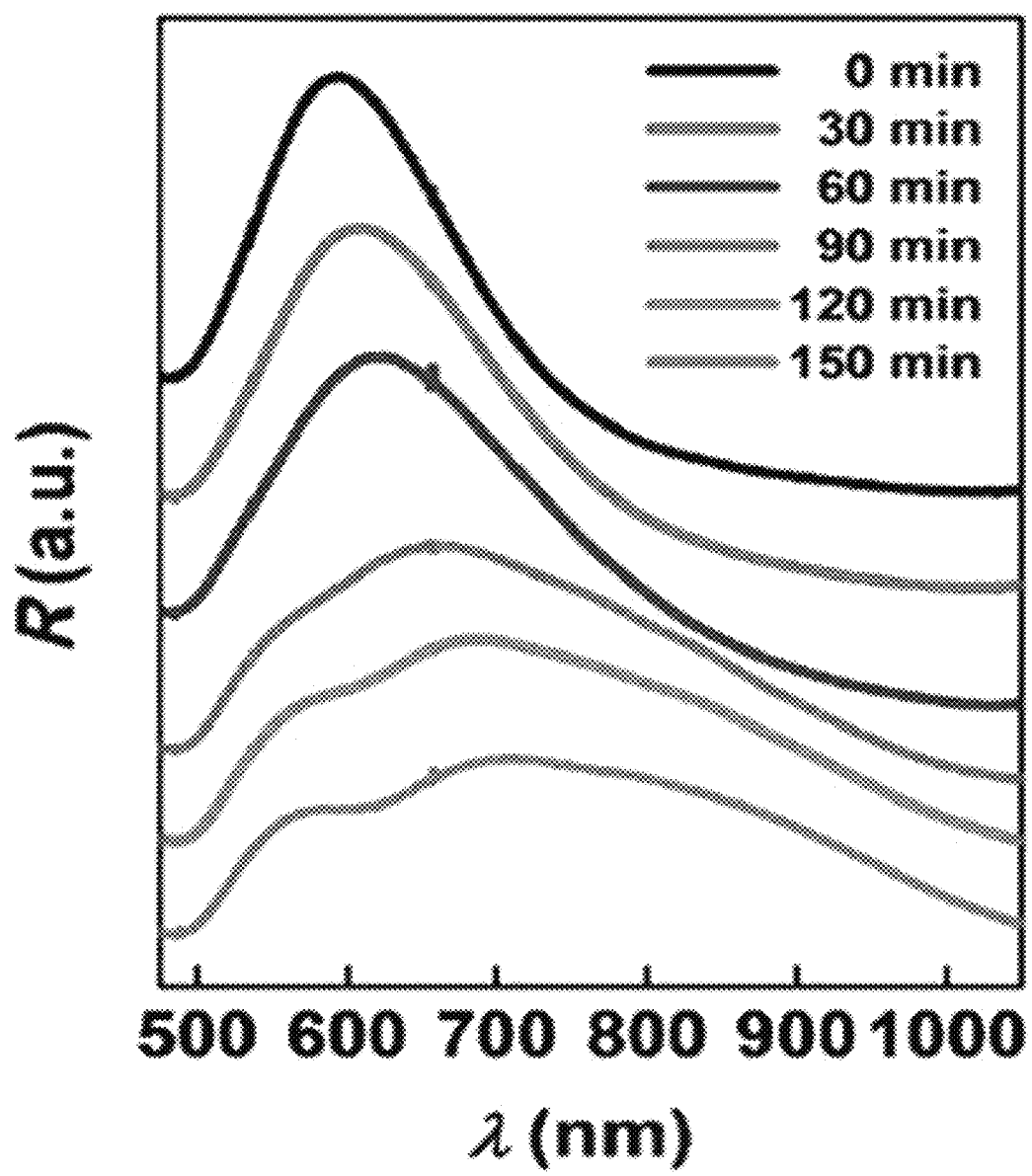

Meanwhile, FIG. 7A and FIG. 7B show the reflectance spectra of the monolayer of gold-core silica-shell nanoparticles (Au@SiO$_2$ nanoparticles) having a silica shell with a thickness of 5.0 nm and transferred to an ITO substrate and glass substrate, respectively, as a function of etching time, wherein the etching time is 0 min., 30 min., 60 min., 90 min., 120 min., and 150 min., as viewed sequentially from the top in each figures.

Figure 7C:
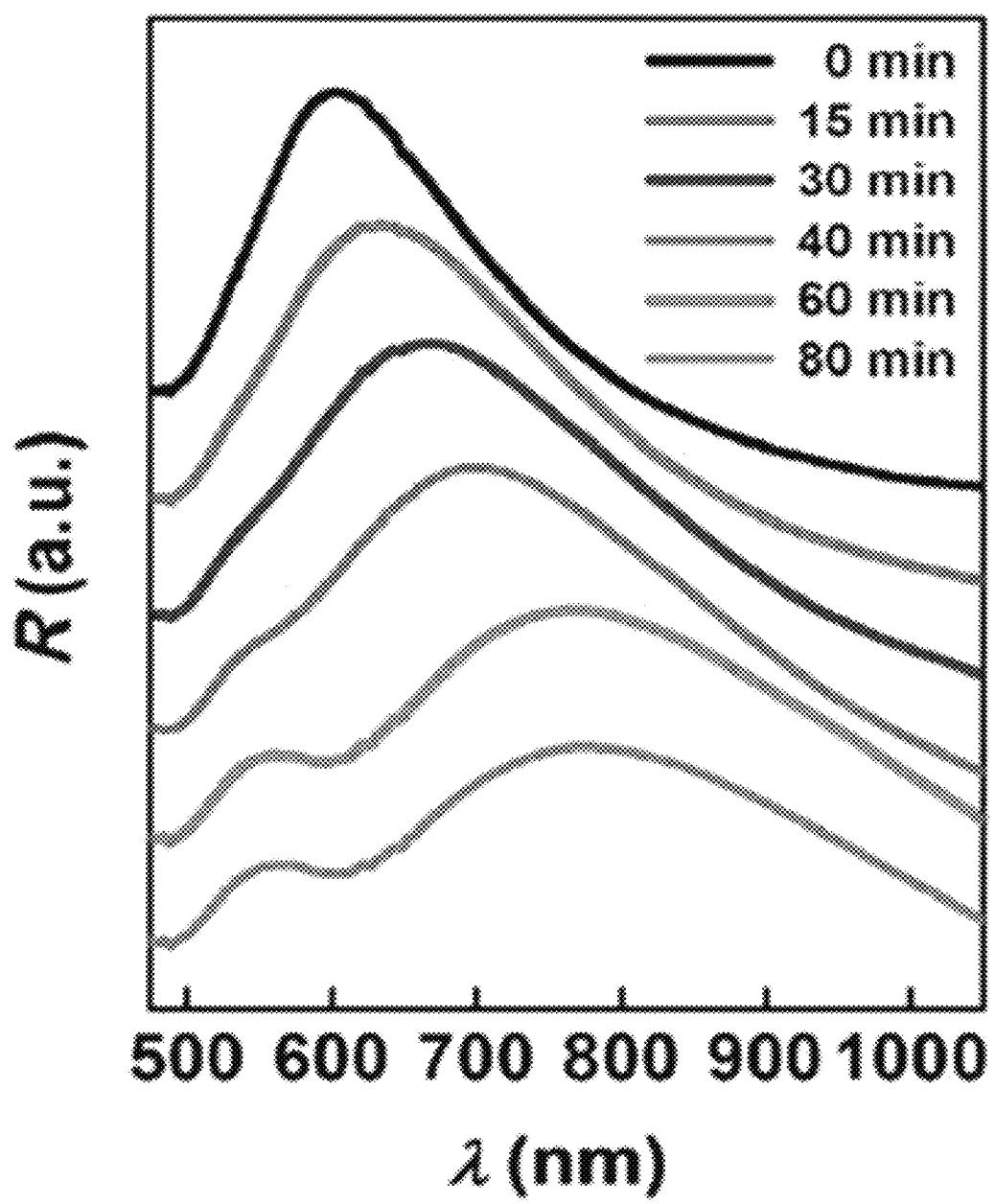
FIG. 7C shows a reflectance spectra of the monolayer of gold-core silica-shell nanoparticles (Au@SiO$_2$ nanoparticles) having a silica shell with a thickness of 2.5 nm and transferred to a glass substrate as a function of etching time in an example, wherein graphs of 0 min., 15 min., 30 min., 40 min., 60 min., and 80 min. are viewed sequentially from the top.

FIG. 7C shows the reflectance spectra of the monolayer of gold-core silica-shell nanoparticles (Au@SiO$_2$ nanoparticles) having a silica shell with a thickness of 2.5 nm and transferred to a glass substrate as a function of etching time, wherein the etching time is 0 min., 15 min., 30 min., 40 min., 60 min., and 80 min., as viewed sequentially from the top.

Two SPR bands in the visible range and near-IR range result from a strong near-field coupling between nanoparticles caused by a decrease in interparticle distance upon removal of silica shells.

From the results showing a decrease in distance between gold core particles depending on shell etching time, it can be seen that in the two cases, the distance between gold core particles is decreased to a level of about 1-2 nm.

Meanwhile, in order to examine the stability of the gold-core silica-shell nanoparticles (Au@SiO$_2$ nanoparticles) to various substrates during etching, FESEM is carried out for each of a glass substrate and ITO substrate and the nanoparticle density is determined before and after etching.

FIG. 8 shows the FESEM results for the cases using a glass substrate and an ITO substrate and the nanoparticle density before and after etching in an example of the present invention. The scale bar in the image of FIG. 8 corresponds to 200 nm.

Figure 8A:
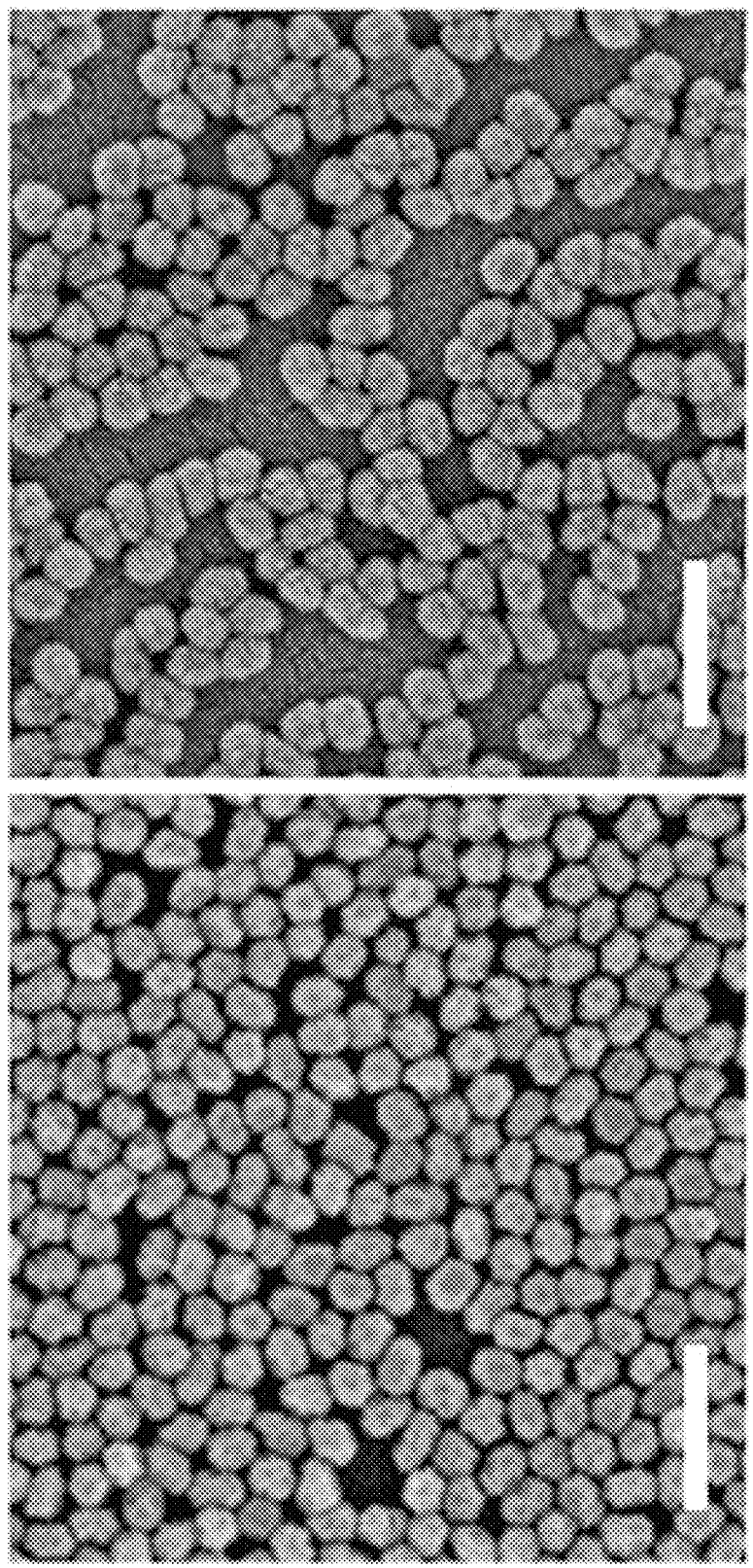
FIG. 8A is an FESEM image of the gold-core silica-shell nanoparticles (Au@SiO$_2$ nanoparticles) having a shell thickness of 5.0 nm after being transferred to a glass substrate in an example, wherein the left-side image shows the nanoparticles before etching and the right-side image shows the nanoparticles after etching.
Figure 8B:
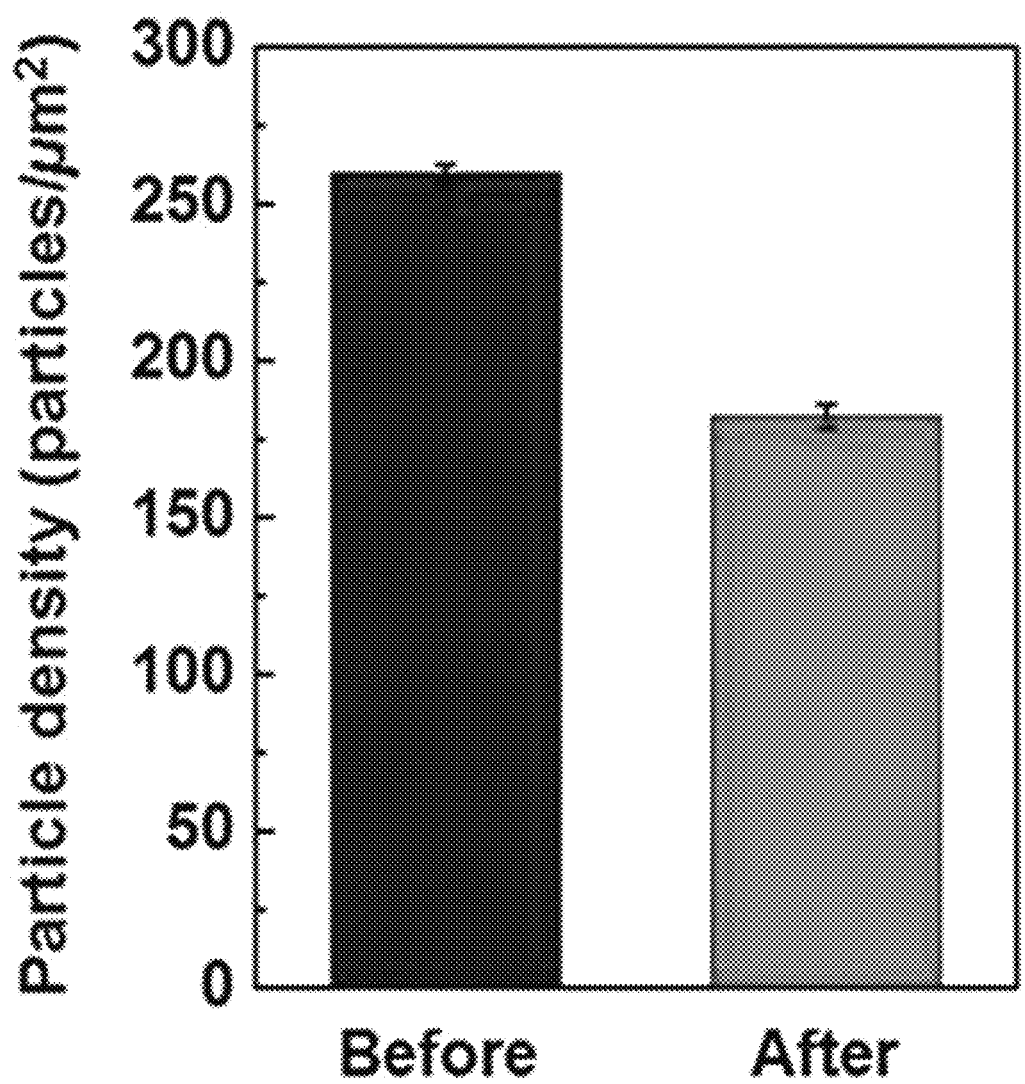
FIG. 8B is a graph illustrating nanoparticle density before etching (left-side) and after etching (right-side) of the gold-core silica-shell nanoparticles (Au@SiO$_2$ nanoparticles) having a shell thickness of 5.0 nm after being transferred to a glass substrate in an example.

Particularly, FIG. 8A is an FESEM image of the gold-core silica-shell nanoparticles (Au@SiO$_2$ nanoparticles) having a shell thickness of 5.0 nm after being transferred to a glass substrate, wherein the left-side image shows the nanoparticles before etching and the right-side image shows the nanoparticles after etching. FIG. 8B is a graph illustrating the nanoparticle density of the gold-core silica-shell nanoparticles (Au@SiO$_2$ nanoparticles) having a shell thickness of 5.0 nm and transferred to a glass substrate, before etching (black) and after etching (gray).

Figure 8C:
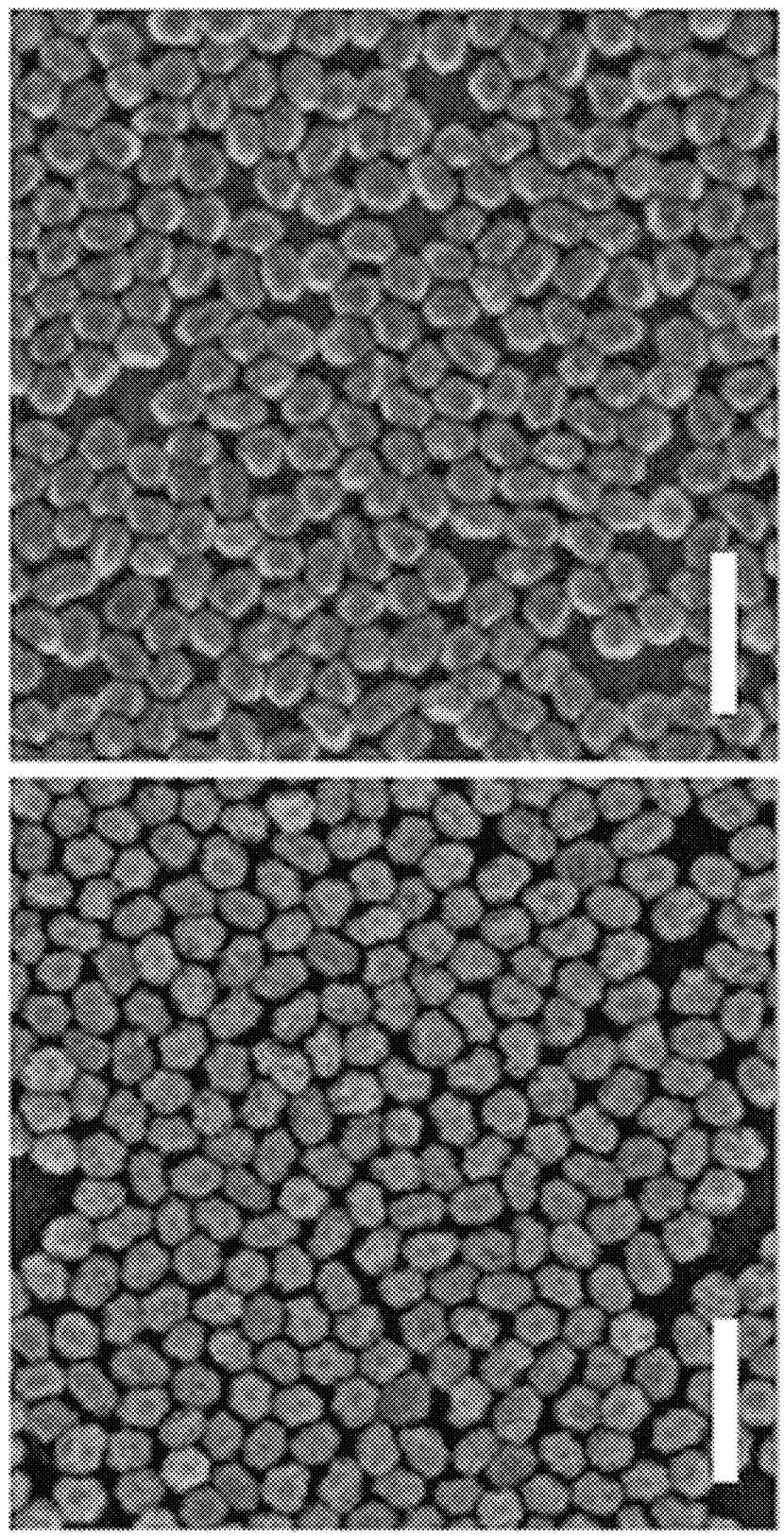
FIG. 8C is an FESEM image of the gold-core silica-shell nanoparticles (Au@SiO$_2$ nanoparticles) having a shell thickness of 5.0 nm after being transferred to an ITO substrate, wherein the left-side is an image showing before etching and the right-side is an image showing after etching in an example.
Figure 8D:
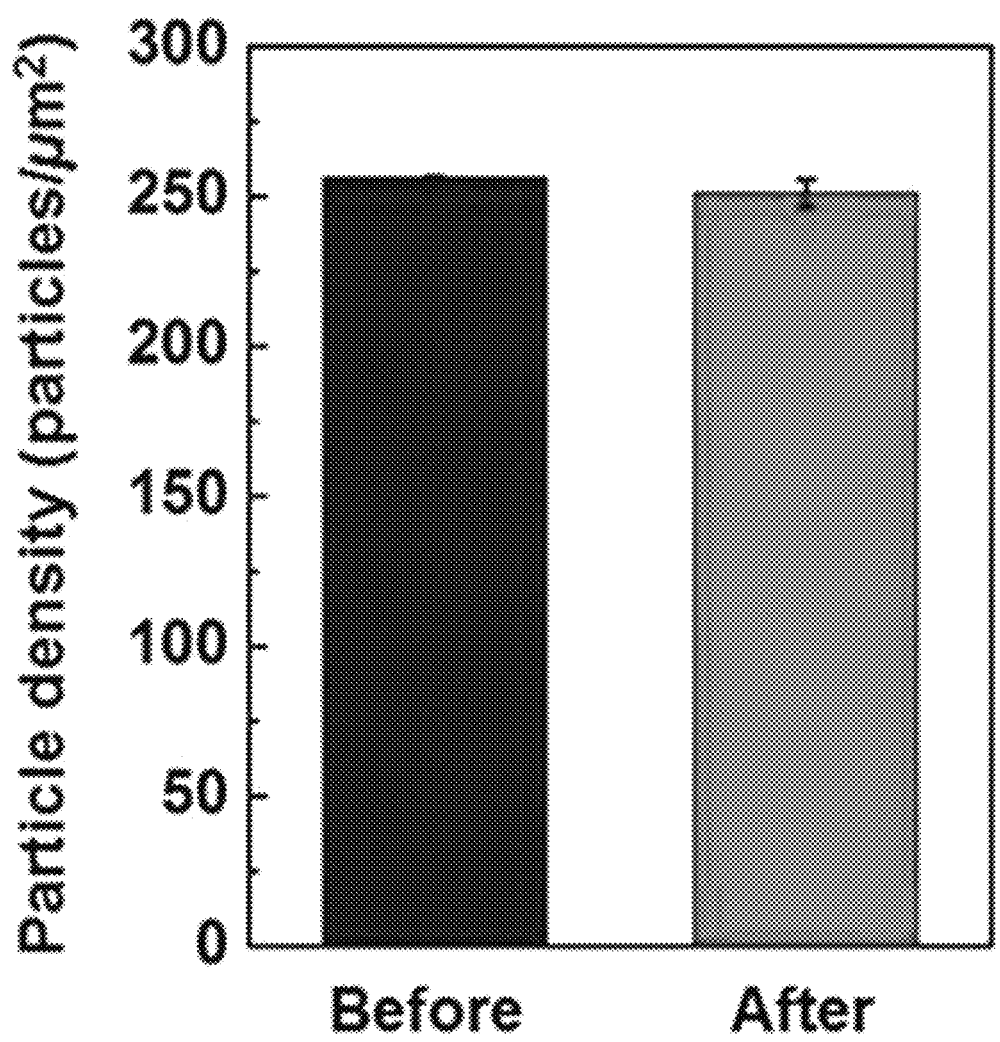
FIG. 8D is a graph illustrating nanoparticle density before etching (left-side) and after etching (right-side) of the gold-core silica-shell nanoparticles (Au@SiO$_2$ nanoparticles) having a shell thickness of 5.0 nm after being transferred to an ITO substrate in an example.

FIG. 8C is an FESEM image of the gold-core silica-shell nanoparticles (Au@SiO$_2$ nanoparticles) having a shell thickness of 5.0 nm after being transferred to an ITO substrate, wherein the left-side image shows the nanoparticles before etching and the right-side image shows the nanoparticles after etching. FIG. 8D is a graph illustrating nanoparticle density of the gold-core silica-shell nanoparticles (Au@SiO$_2$ nanoparticles) having a shell thickness of 5.0 nm and transferred to an ITO substrate, before etching (black) and after etching (gray).

Herein, the nanoparticle density corresponds to the number of nanoparticles per unit area (1 square micrometer) and is measured by randomly selecting unit areas at 5 locations.

The average particle loss ratio is about 29% in the case of the glass substrate and about 2% in the case of the ITO substrate. The standard deviation (standard deviation based on average number density per unit area) is 3.7% and 3.1%, respectively.

4. Determination of Raman Signals—Molecular Sensing Method

To determine the advantages of the nanogap structures having voids obtained from the exemplary embodiments of the present invention, the nanogap structures are applied to surface enhanced Raman spectroscopy (SERS) that is an ultrasensitive analysis technology and Raman signals of various analyte molecules are detected.

As a Raman sensing probe, Rhodamine 6G (R6G), BPE (1,2-bis(4-pyridyl)ethylene) or adenine is used. To 100 µL of each solution, the substrate is exposed at a different concentration as described hereinafter. Several minutes after the exposure, SERS spectra are obtained and at least 10 locations selected randomly from the substrate are subjected to SERS. The SERS spectra are obtained by using a 785 nm laser at 250 mW and the integration time is 3 seconds.

Figure 9A:
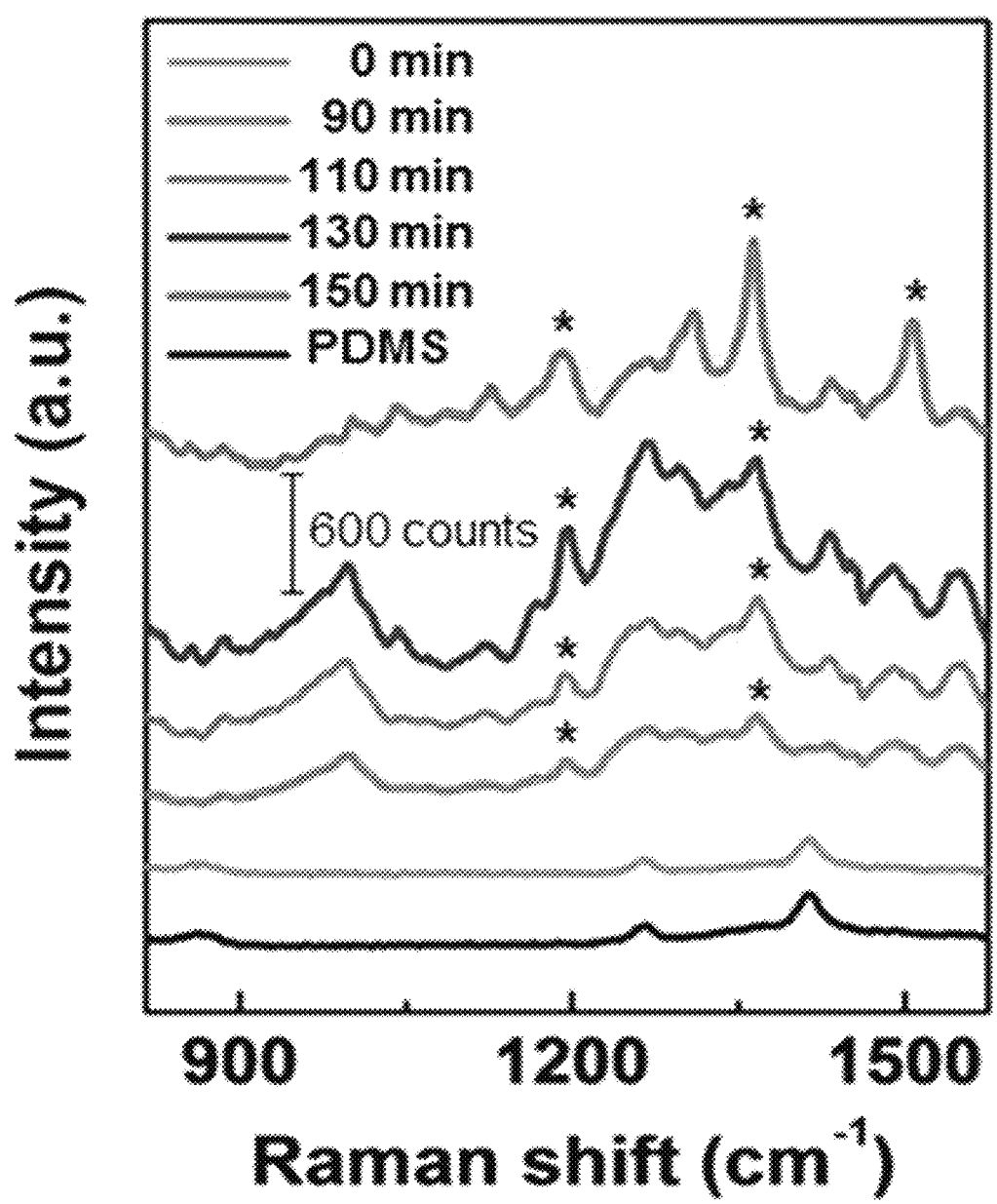
Figure 9B:
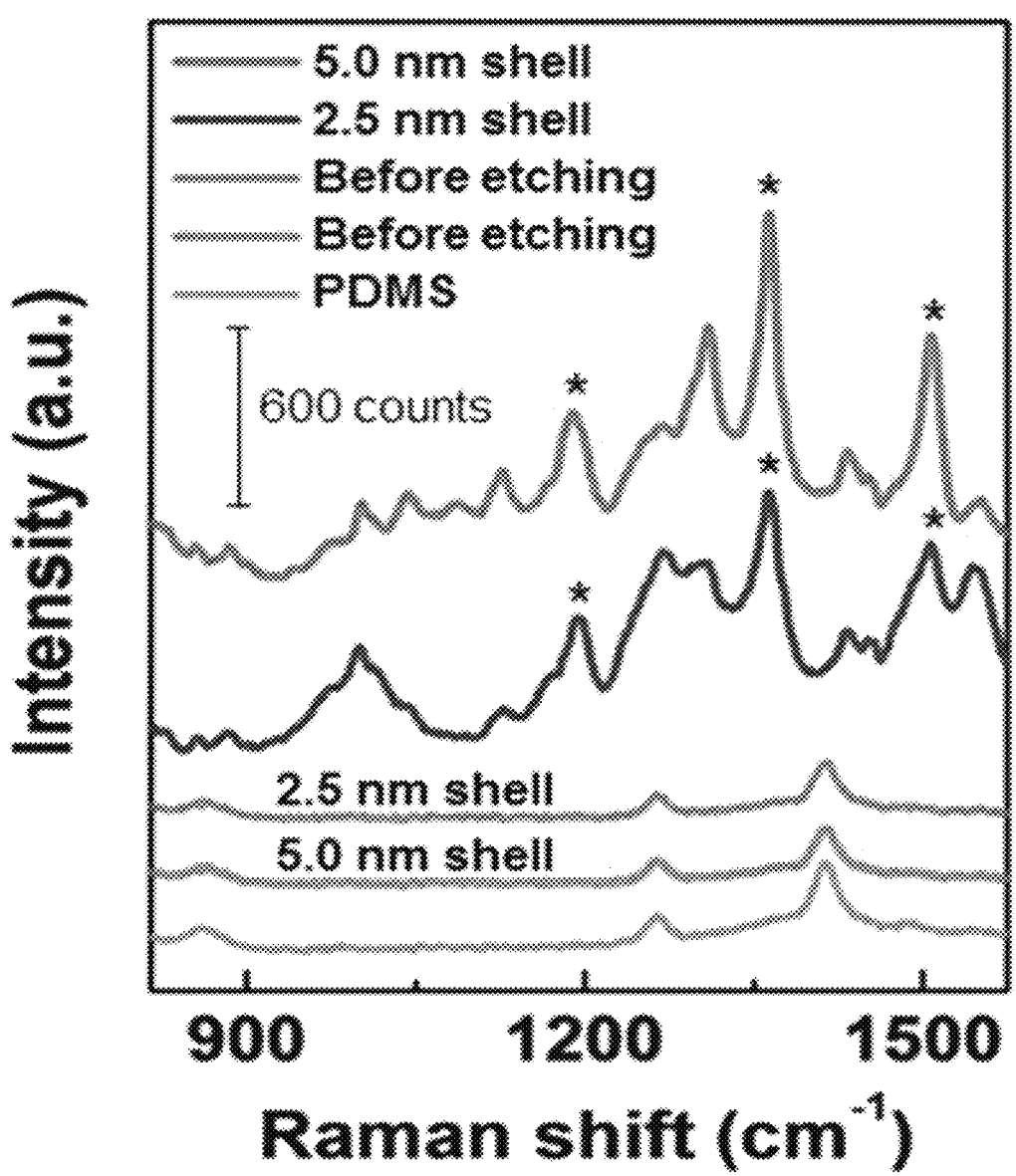

FIG. 9A and FIG. 9B show SERS signals of the monolayer of gold-core silica-shell nanoparticles (Au@SiO$_2$ nanoparticles) on PDMS before and after the silica etching (1 µM R6G). In FIG. 9A, SERS signals of 0 min., 90 min., 110 min., 130 min., 150 min., and PDMS are viewed sequentially from the top. In FIG. 9B, SERS signals of 5.0 nm shell, 2.5 nm shell, Before etching (2.5 nm shell), Before etching (5.0 nm shell) and PDMS are viewed sequentially from the top.

In the case of the gold-core silica-shell nanoparticles (Au@SiO$_2$ nanoparticles) on PDMS before etching, no clear SERS peak appears for 1 µM of Rhodamine 6G (R6G). However, as etching proceeded, the Raman peaks of R6G become significant and the intensities at 1192 cm$^{-1}$, 1363 cm$^{-1}$ and 1507 cm$^{-1}$ are increased (see the asterisks of FIG. 9A and FIG. 9B). FIG. 9B shows signal enhancement after silica shell etching.

Figure 9C:
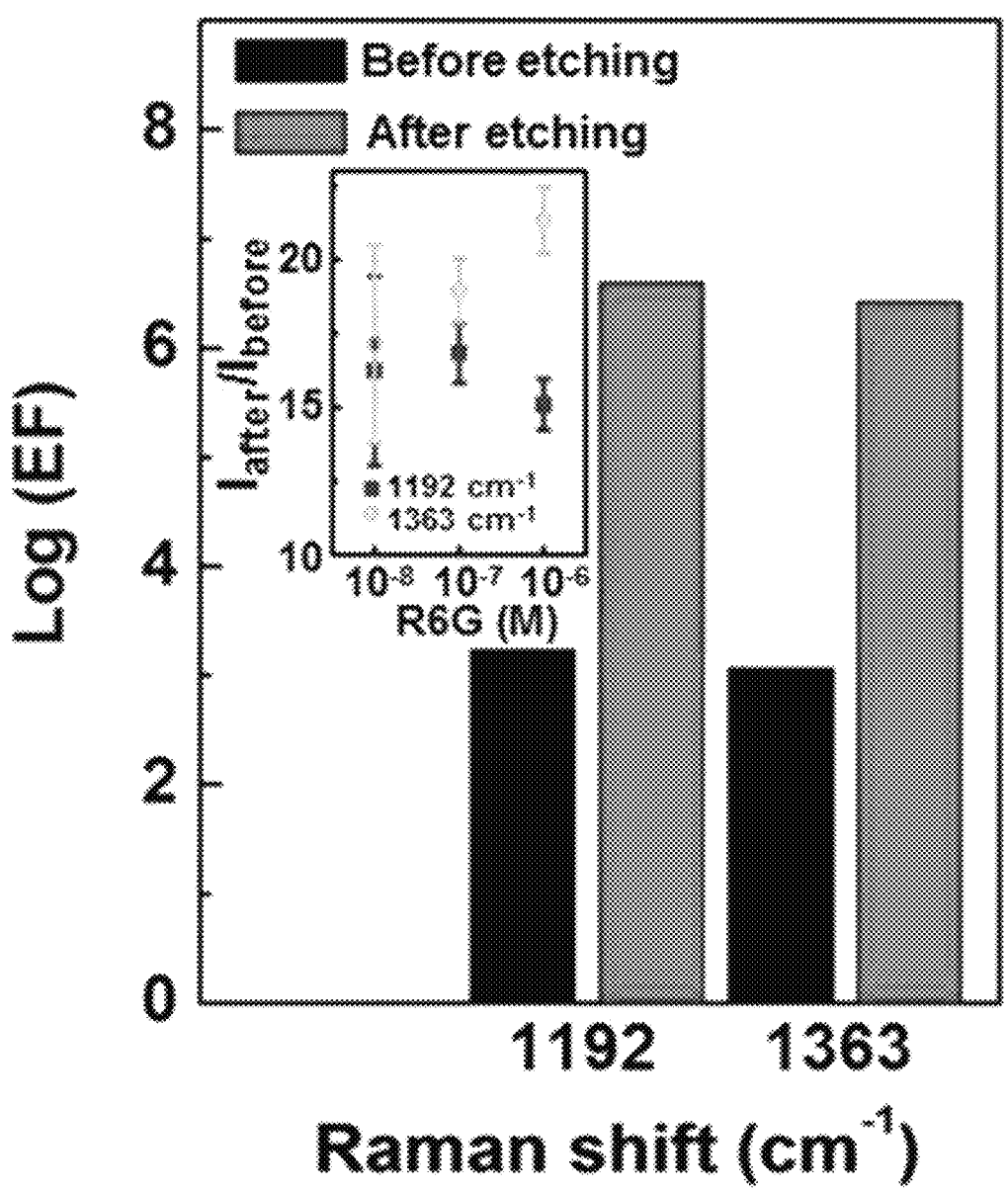
FIG. 9C is a graph illustrating the Raman EF measured from the monolayer of gold-core silica-shell nanoparticles (Au@SiO$_2$ nanoparticles) before etching as compared to the monolayer after etching.

FIG. 9C is a graph illustrating the Raman EF measured from the monolayer of gold-core silica-shell nanoparticles (Au@SiO$_2$ nanoparticles) before etching as compared to the monolayer after etching.

The enhancement factors (EF) before and after etching are 10$^3$ and 10$^6$, respectively, and thus the EF improvement (additional EF) is about 1,000-10,000, which is caused by the strong field enhancement and free diffusion of analyte molecules positioned near the void nanogaps. That is, such improvement of accessibility of molecules to the void nanogaps results in an increase in number of molecules participating in the SERS process. Herein, after carrying out etching for 150 minutes, no change in surface plasmonic resonance band are observed. Thus, etching time is set to 150 minutes and the smallest void gap is also obtained at an etching time of 150 minutes.

Figure 9D:
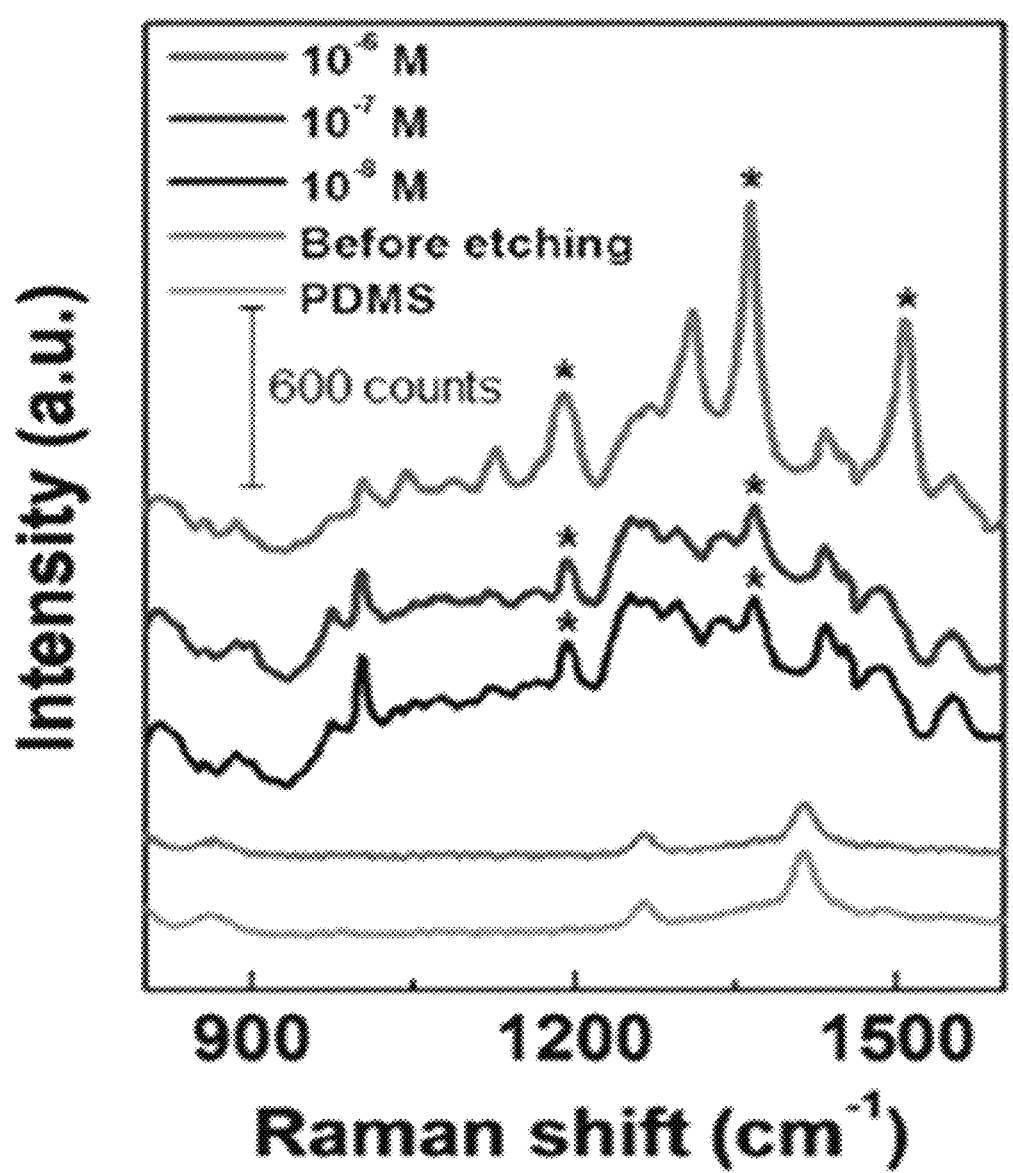
FIG. 9D shows SERS signals of the gold-core silica-shell nanoparticles (Au@SiO$_2$ nanoparticles) (silica shell thickness 5.0 nm) before etching and the particles obtained after chemical etching for 150 minutes at a different concentration of 1 μM, 100 nM and 10 nM of R6G in an example, wherein the SERS signals of 1 μM, 100 nM, 10 nM, Before etching and PDMS are viewed sequentially from the top.

FIG. 9D shows SERS signals of the gold-core silica-shell nanoparticles (Au@SiO$_2$ nanoparticles) (silica shell thickness 5.0 nm) before etching and the particles obtained after chemical etching for 150 minutes at a different concentration of 1 µM, 100 nM and 10 nM of R6G in an example of the present invention, wherein SERS signals of 1 µM, 100 nM, 10 nM, Before etching and PDMS are viewed sequentially from the top.

Figure 9E:
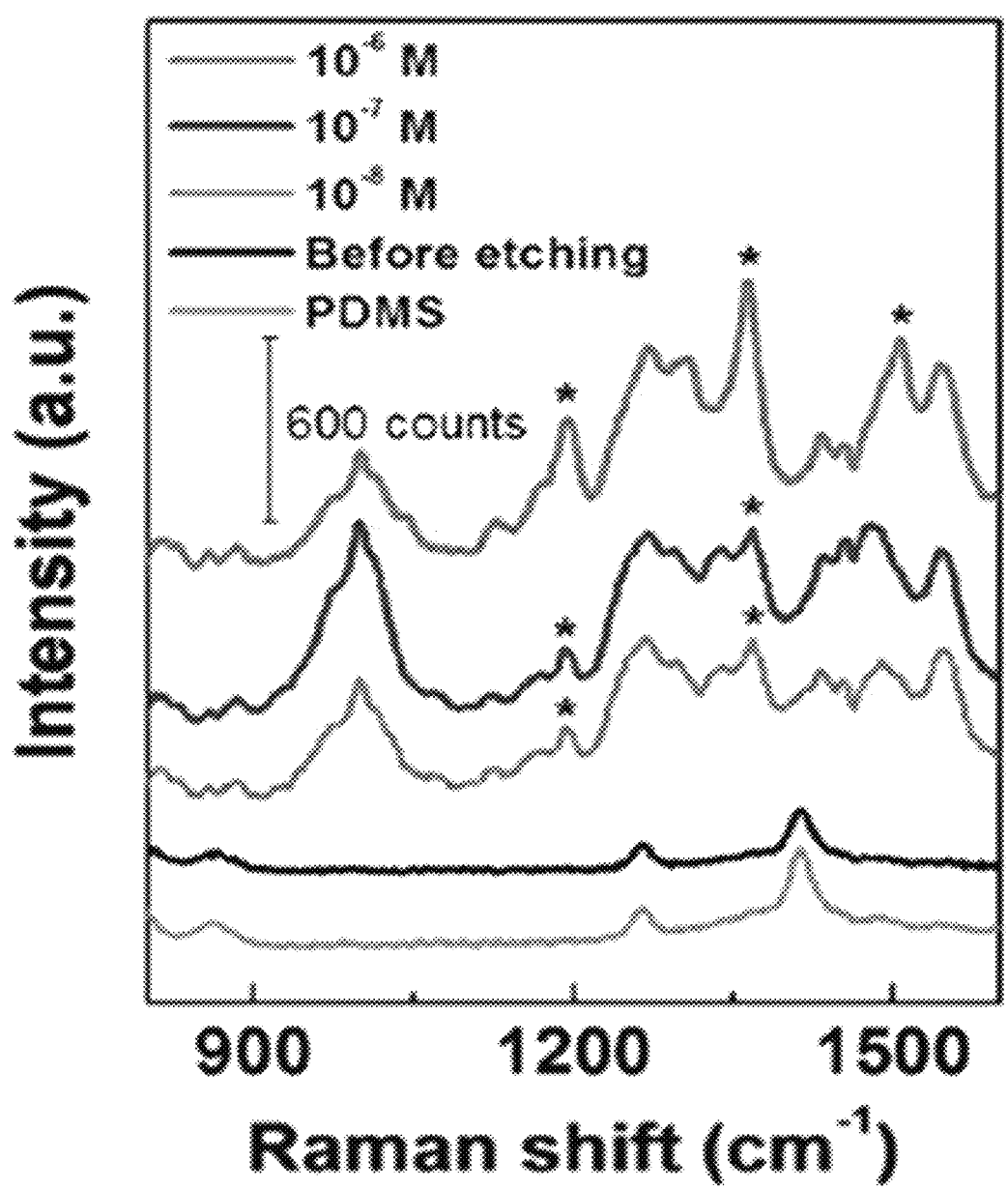
FIG. 9E shows SERS signals of the gold-core silica-shell nanoparticles (Au@SiO$_2$ nanoparticles) (silica shell thickness 2.5 nm) before etching and the particles obtained after chemical etching for 150 minutes at a different concentration of 1 μM, 100 nM and 10 nM of R6G in an example, wherein the SERS signals of 1 μM, 100 nM, 10 nM, Before etching and PDMS are viewed sequentially from the top.

FIG. 9E shows SERS signals of the gold-core silica-shell nanoparticles (Au@SiO$_2$ nanoparticles) (silica shell thickness 2.5 nm) before etching and the particles obtained after chemical etching for 150 minutes at a different concentration of 1 µM, 100 nM and 10 nM of R6G in an example of the present invention, wherein the SERS signals of 1 µM, 100 nM, 10 nM, Before etching and PDMS, are viewed sequentially from the top.

In the graphs of FIG. 9D and FIG. 9E, the peaks marked with asterisks correspond to the Raman peaks at the bands of 1192 cm$^{-1}$, 1363 cm$^{-1}$ and 1507 cm$^{-1}$, respectively. It can be seen that SEFS signals are observed well at different concentrations after etching.

Meanwhile, versatility of the exemplary embodiments of the present invention is further checked.

Figure 9F:
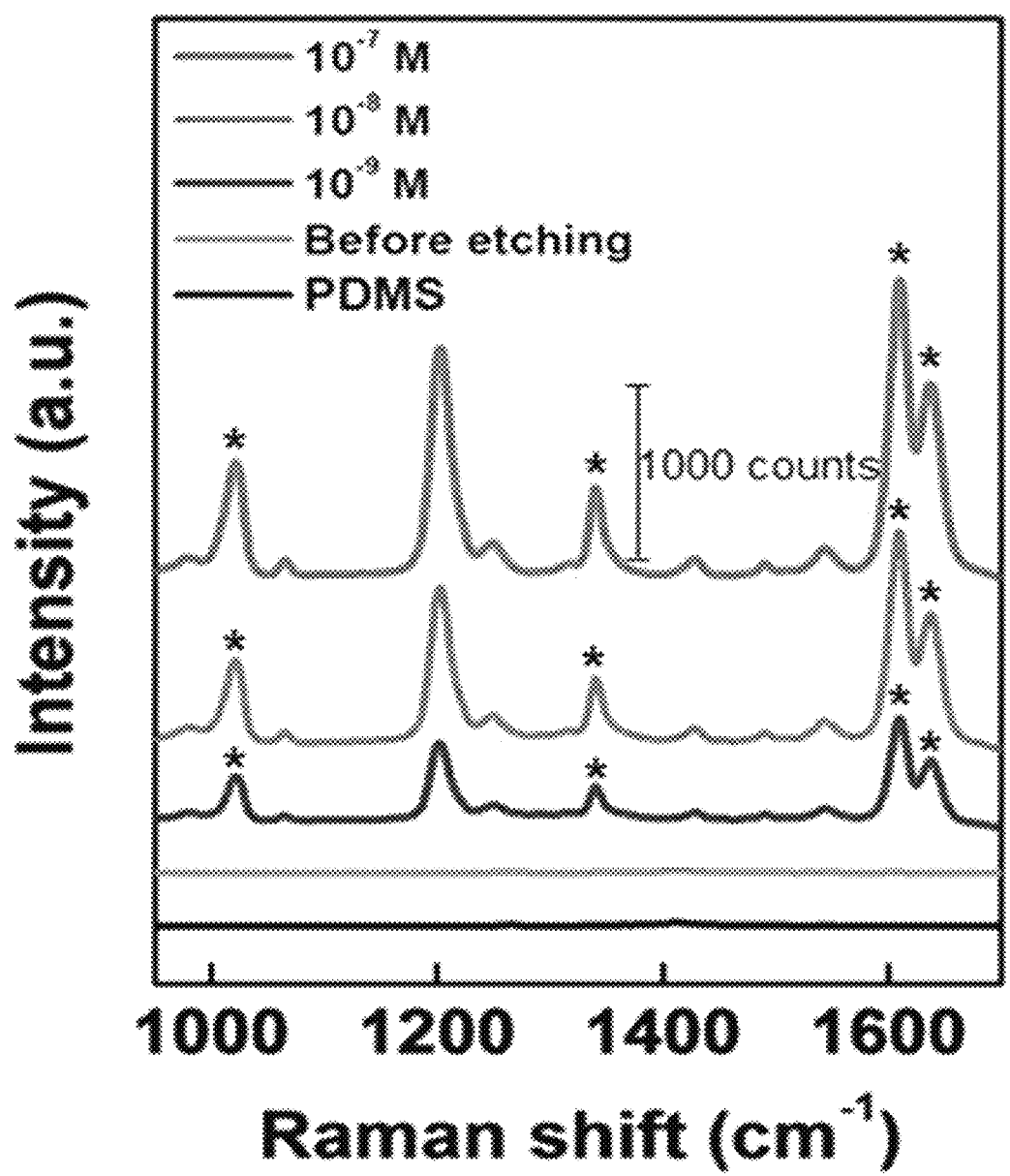
FIG. 9F shows SERS signals obtained after chemical etching for 150 minutes at a different concentration of 100 nM, 10 nM and 1 nM of BPE in an example, wherein the SERS signals of 100 nM, 10 nM, 1 nM, Before etching and PDMS are viewed sequentially from the top.

FIG. 9F shows SERS signals obtained after chemical etching for 150 minutes at a different concentration of 100 nM, 10 nM and 1 nM of BPE (1,2-bis(4-pyridyl)ethylene) in an example of the present invention, wherein SERS signals of 100 nM, 10 nM, 1 nM, Before etching and PDMS, are viewed sequentially from the top.

In the graph of FIG. 9F, the peaks marked with asterisks correspond to the Raman peaks at the bands of 1021 cm$^{-1}$, 1340 cm$^{-1}$, 1611 cm$^{-1}$ and 1638 cm$^{-1}$, respectively. It can be seen that when using BPE as a Raman sensing probe, SEFS signals are also observed well.

Figure 9G:
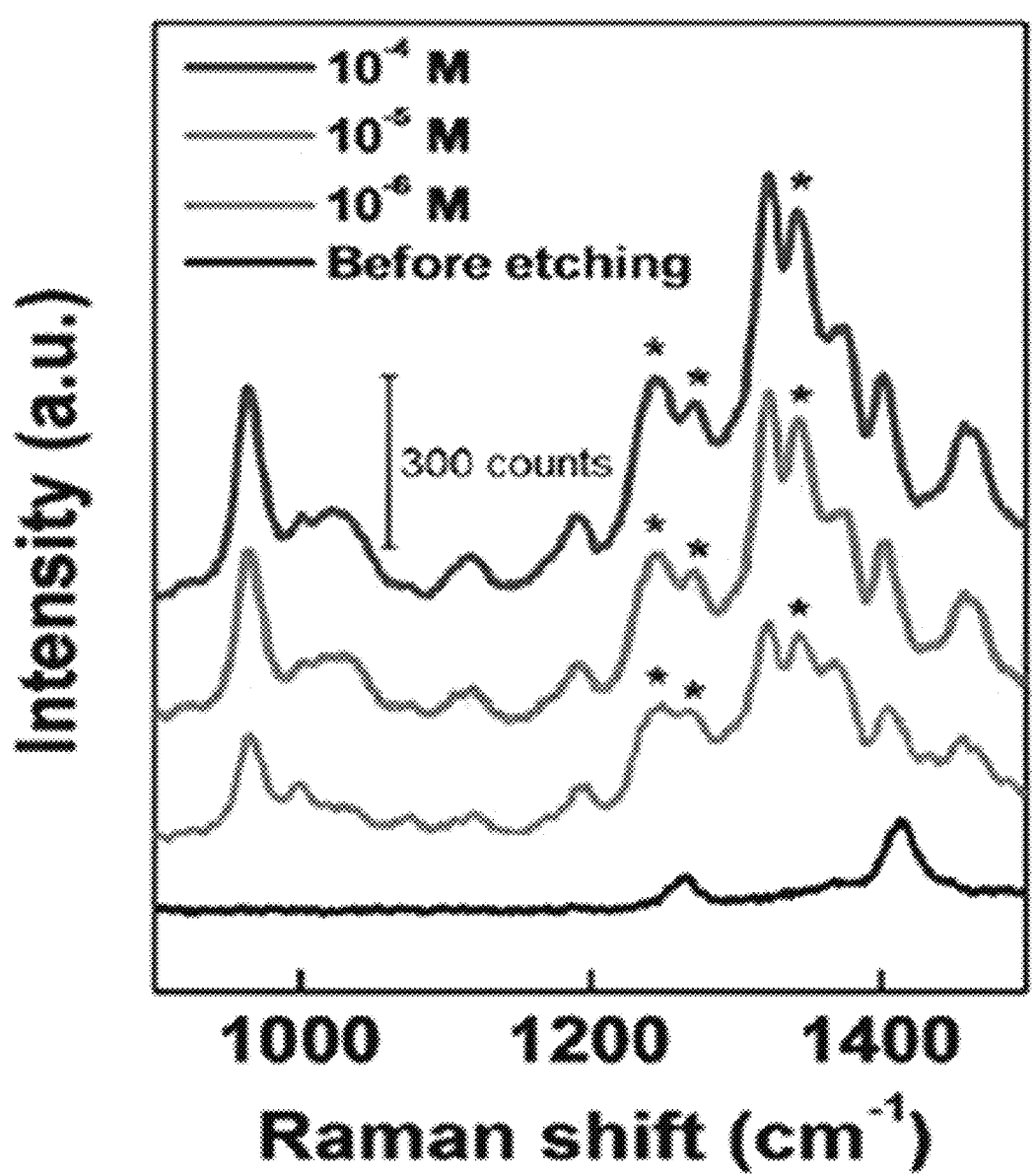
FIG. 9G shows SERS signals of particles obtained after chemical etching for 150 minutes at a different concentration of 100 μM, 10 μM and 1 μM of adenine in an example, wherein the SERS signals of 100 μM, 10 μM and 1 μM and Before etching are viewed sequentially from the top.

FIG. 9G shows SERS signals of particles obtained after chemical etching for 150 minutes at a different concentration of 100 µM, 10 µM and 1 µM of adenine in an example of the present invention, wherein the SERS signals of 100 µM, 10 µM and 1 µM and Before etching are viewed sequentially from the top.

In the graph of FIG. 9G, the peaks marked with asterisks correspond to the Raman peaks at the bands of 1244 cm$^{-1}$, 1273 cm$^{-1}$ and 1344 cm$^{-1}$, respectively. It can be seen that when using adenine as a Raman sensing probe, SEFS signals are also observed well.

Meanwhile, in order to test the reproducibility of exemplary embodiments of the present invention, examples are again prepared using ten different substrates.

FIG. 10 shows SERS signals and intensities measured when using 10 different substrates to test the reproducibility in an example of the present invention.

Figure 10A:
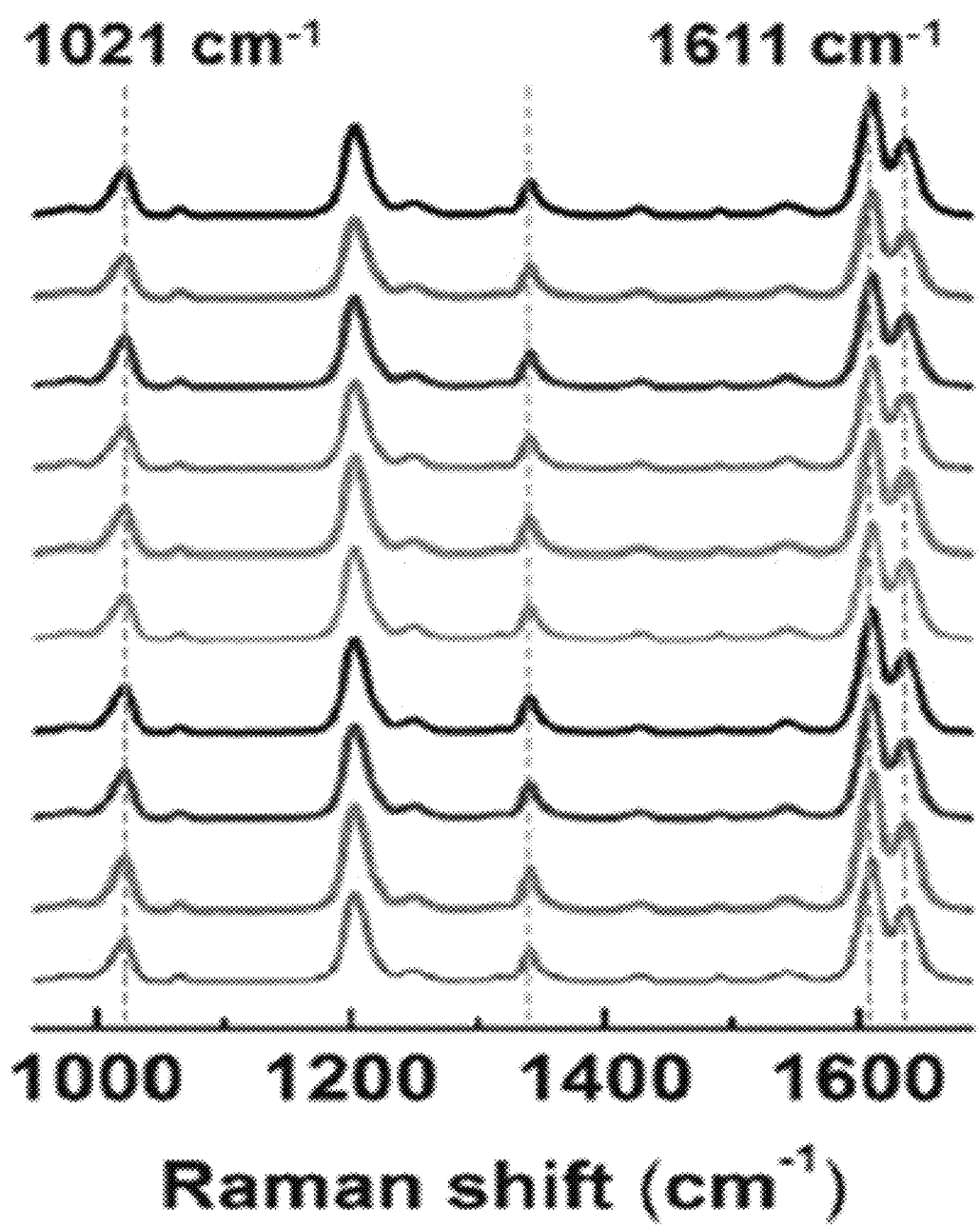
FIG. 10A shows SERS signals of the monolayer of 10 gold-core silica-shell nanoparticles (Au@SiO$_2$ nanoparticles), in which silica shell thickness is 5.0 nm, transferred to PDMS after etching for 150 minutes at 1 μM of BPE in an example.
Figure 10B:
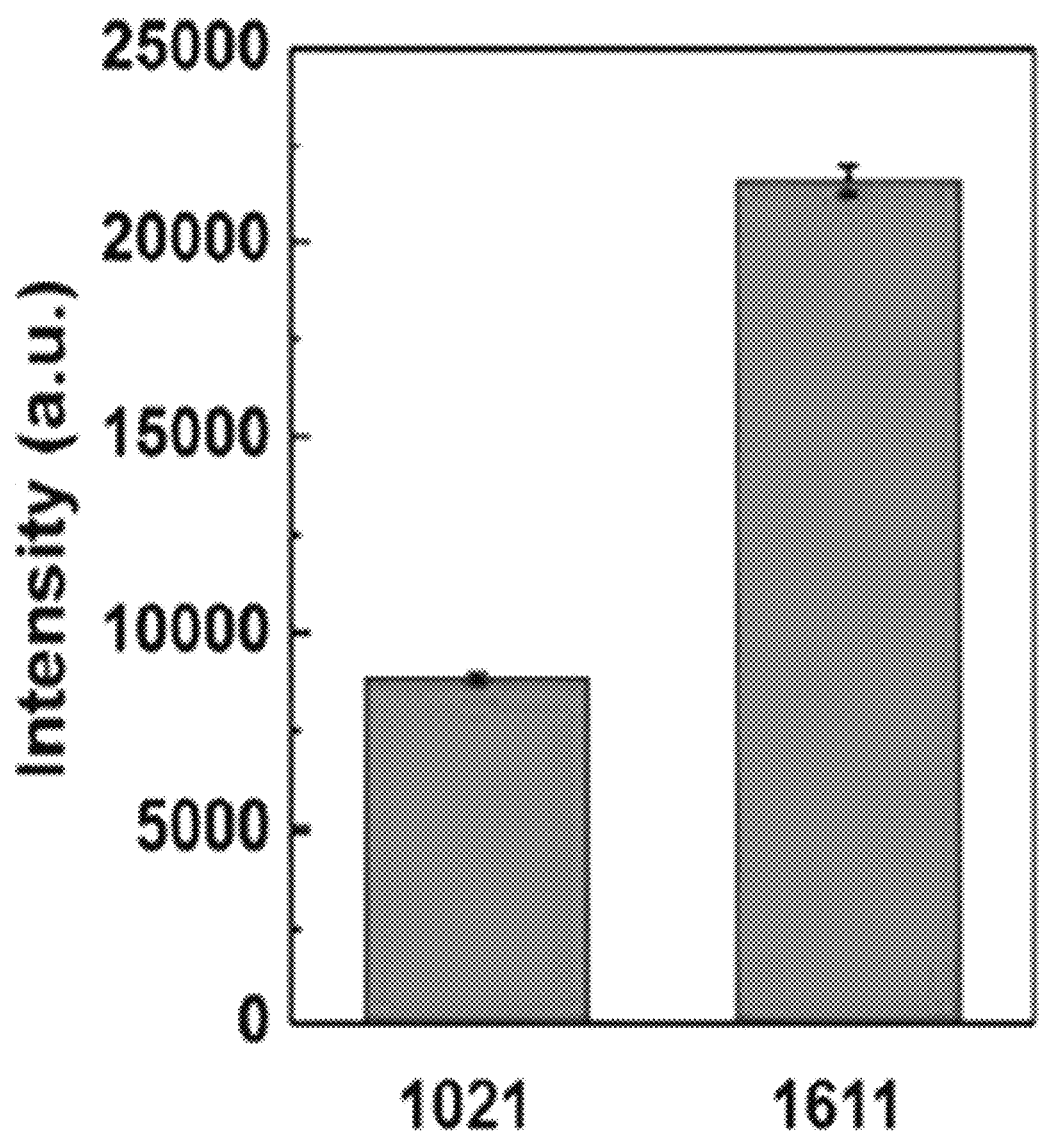
FIG. 10B shows an intensity of each band of Raman signals of 1 μM BPE.
Figure 10C:
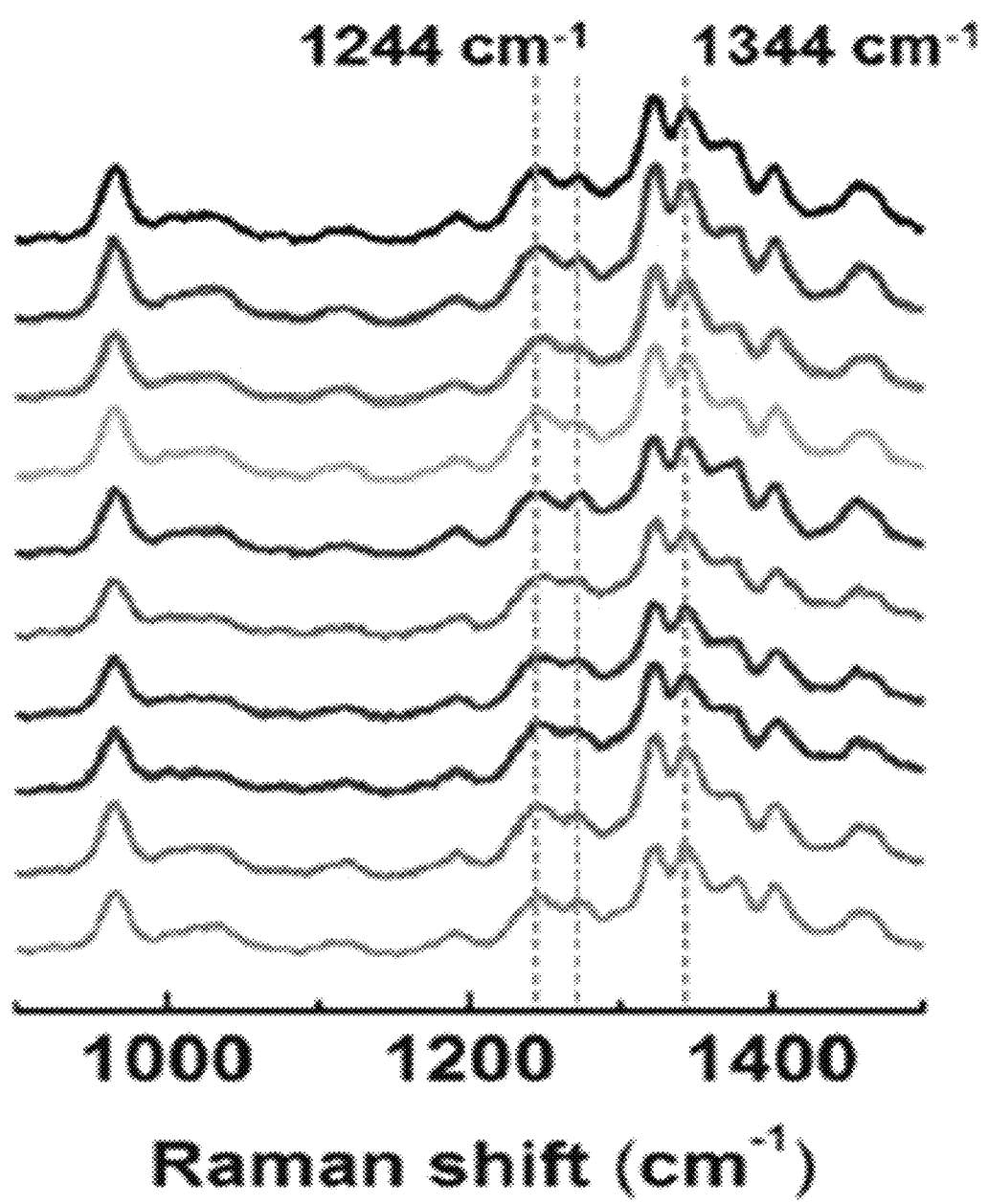
FIG. 10C shows SERS signals of the monolayer of 10 gold-core silica-shell nanoparticles (Au@SiO$_2$ nanoparticles), in which silica shell thickness is 5.0 nm, transferred to PDMS after etching for 150 minutes at 10 μM of adenine in an example.
Figure 10D:
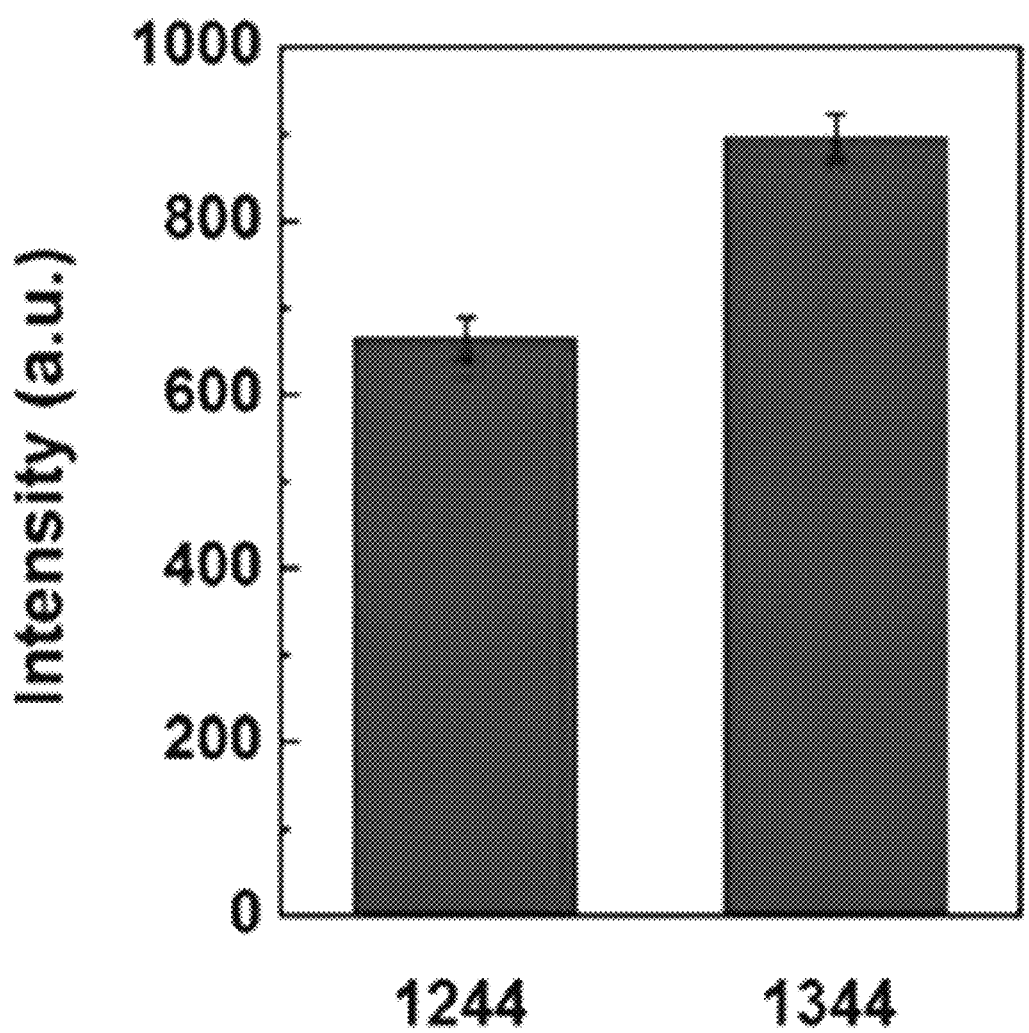
FIG. 10D shows an intensity of each band of Raman signals of 10 μM adenine.

Particularly, FIG. 10A and FIG. 10C show SERS signals of the monolayer of 10 gold-core silica-shell nanoparticles (Au@SiO$_2$ nanoparticles) (silica shell thickness 5.0 nm) transferred to PDMS after etching for 150 minutes at 1 µM of BPE (FIG. 10A) and at 10 µM of adenine (FIG. 10C) in an example of the present invention. In addition, FIG. 10B shows the intensity of each band of Raman signals of 1 µM BPE, and FIG. 10D shows the intensity of each band of Raman signals of 10 µM adenine. In FIG. 10B and FIG. 10D, SERS signal intensities are substantially the same and show a very small standard deviation (standard deviation based on average SERS signals). Particularly, the standard deviations of SERS intensities at the bands of 1 µM of BPE of 1021 cm$^{-1}$ and 1611 cm$^{-1}$ in FIG. 10B are 5.0% and 5.6%, respectively. The standard deviations of SERS intensities at the bands of 10 µM of adenine of 1244 cm$^{-1}$ and 1344 cm$^{-1}$ in FIG. 10D are 12% and 9.7%, respectively.

As can be seen from the foregoing, the ten substrates show substantially the same SERS signals. This demonstrates very high reproducibility of exemplary embodiments of the present invention.

As described above, in exemplary embodiments of the present invention, a layer of nanoparticles having metal cores and shells is formed, for example, by self-assembly, and then transferred to a substrate. Then, the shells are removed to form ultrasmall voids between metal core particles and nanogaps are provided by the voids. It can be seen from near-field coupling (reflectance analysis) and FESEM images that the interparticle distance is reduced more after the shells are removed. Further, it can be also seen that it is possible to obtain strong SERS signals to Raman dyes and/or biomolecules uniformly with high reproducibility from the ultrasmall void nanogap structures, which, otherwise, cannot be obtained from the monolayer of gold-silica core-shell nanoparticles. Further, it can be seen from the surface enhancement Raman scattering test that such an additional enhancement factor (e.g. an additional enhancement factor of about 1,000-10,000) obtained from the nanogap structure results from the near-field enhancement and the free diffusion of molecules close to the void nanogaps.

What is claimed is:

1. A method for preparing a nanogap structure, comprising:
   providing nanoparticles, each of said nanoparticles consisting of a metal core and a shell surrounding the core; and
   removing the shell from each of said nanoparticles to obtain metal particles and to form a void between the metal particles,
   wherein, in the nanogap structure, the metal particles consist of a metal without a linker molecule including DNA attached to the metal at outside of the metal; and
   wherein a nanogap of the nanogap structure is provided by the void, and
   wherein analyte molecules in the nanogap provided by the void freely diffuse without a limitation which is caused by the linker molecule,
   wherein the nanogap provided by the void shows a near-field enhancement, and
   wherein the removed shell consists of at least one selected from the group consisting of Au, Ag, Cu, Pt, Pd, Si (silicon), $SiO_2$ (silica), Al, $Al_2O_3$ (aluminum oxide), PS (polystyrene), Ti (titanium) and $TiO_2$ (titanium dioxide).

2. The method according to claim 1, comprising:
   forming a monolayer of the nanoparticles;
   transferring the monolayer to a substrate; and
   removing the shell from the nanoparticles disposed on the substrate by way of etching.

3. The method according to claim 2,
   wherein the monolayer of the nanoparticles is formed by self-assembly at an air/liquid interface.

4. The method according to claim 3,
   wherein the monolayer of the nanoparticles is formed by:
   introducing the nanoparticles to a mixture of hexane and water forming an interface;
   adding ethanol thereto; and
   evaporating hexane to form the monolayer of the nanoparticles at the air/water interface.

5. The method according to claim 2,
   wherein the nanoparticles have a close-packed structure in the monolayer.

6. The method according to claim 2,
   wherein the etching is at least one selected from chemical etching, ion beam etching and electron beam etching.

7. The method according to claim 2,
   wherein the etching is a chemical etching wherein a basic solution is provided to etch.

8. The method according to claim 1,
   wherein the metal particles consist of at least one metal selected from the group consisting of Au, Ag, Cu, Pt and Pd.

9. The method according to claim 8,
   wherein the metal particles have a diameter of 10-150 nm.

10. The method according to claim 1,
    wherein the shells have a size of 1-20 nm the void has a size of 1-2 nm.

11. The method according to claim 1,
    wherein the substrate is a solid substrate.

12. The method according to claim 11,
    wherein the substrate is selected from the group consisting of a PDMS (polydimethylsiloxane) substrate, PMMA (poly(methylmethacrylate)) substrate, PS (polystyrene) substrate, Si (silicon) substrate, Ge (germanium) substrate, glass substrate and ITO (Indium tin oxide) substrate.

13. The method according to claim 11,
    wherein the solid substrate is chemically modified to improve a binding force with the nanoparticles.

* * * * *